US 6,692,489 B1
Heim et al.
Feb. 17, 2004

(54) ELECTROSURGICAL MODE CONVERSION SYSTEM

(75) Inventors: Warren P. Heim, Boulder, CO (US); James L. Brassell, Boulder, CO (US); Michael D. Olichney, Lyons, CO (US)

(73) Assignee: Team Medical, LLC, Boulder, CO (US)

( * ) Notice: Subject to any disclaimer, the term of this patent is extended or adjusted under 35 U.S.C. 154(b) by 0 days.

(21) Appl. No.: 09/619,919

(22) Filed: Jul. 20, 2000

Related U.S. Application Data

(60) Provisional application No. 60/144,946, filed on Jul. 21, 1999.

(51) Int. Cl.[7] .............................................. A61B 18/18
(52) U.S. Cl. ........................................................ 606/34
(58) Field of Search ..................... 606/32–35, 37–42; 607/101–102

(56) References Cited

U.S. PATENT DOCUMENTS

| | | | |
|---|---|---|---|
| 4,092,986 A | 6/1978 | Schneiderman | |
| 4,114,623 A | 9/1978 | Meinke et al. | |
| 5,267,997 A | 12/1993 | Farin et al. | |
| 5,318,563 A | 6/1994 | Malis et al. | |
| 5,370,645 A | 12/1994 | Klicek et al. | 606/35 |
| 5,472,442 A | 12/1995 | Klicek | 606/42 |
| 5,472,443 A | 12/1995 | Cordis et al. | 606/48 |
| 5,540,681 A | 7/1996 | Strul et al. | |
| 5,633,578 A * | 5/1997 | Eggers et al. | 606/38 |
| 5,693,045 A * | 12/1997 | Eggers | 606/32 |
| 5,697,909 A | 12/1997 | Eggers et al. | 604/114 |
| 5,766,153 A | 6/1998 | Eggers et al. | 604/114 |
| 5,833,686 A | 11/1998 | Zhao | 606/34 |
| 5,891,095 A | 4/1999 | Eggers et al. | 604/114 |
| 6,074,387 A * | 6/2000 | Heim et al. | 606/34 |

FOREIGN PATENT DOCUMENTS

WO    WO 98/47436    * 10/1998    ................ 606/32

OTHER PUBLICATIONS

Serway, Raymond; Physics for Scientists and Engineers pp. 746–755.*

* cited by examiner

*Primary Examiner*—Michael Peffley
(74) *Attorney, Agent, or Firm*—Marsh Fischmann & Breyfogle LLP

(57) ABSTRACT

A surgical system that applies electrical energy to obtain predetermined surgical effects while improving the control of the application of the energy that is supplied by electrosurgical generators. In one embodiment, a surgical assembly interfaces with and receives power from an electrosurgical generator for executing a first electrosurgical procedure. This surgical assembly may employ a shunt circuit between its power and return lines for providing in effect a voltage limitation and/or to allow a constant power electrosurgical generator to execute an at least substantially constant voltage electrosurgical technique. The electrosurgical assembly may also include a return coupler for directing energy from the patient back to the electrosurgical generator, which in turn may include a dielectric material which interfaces with the patient and which at least initially conveys the return energy via one or more electric fields versus conduction.

20 Claims, 14 Drawing Sheets

ELECTROSURGICAL MODE CONVERSION SYSTEM

RELATED APPLICATIONS

This patent application claims priority from U.S. Provisional Patent Application No. 60/144,946, filed on Jul. 21, 1999, and entitled "SURGICAL MODE CONVERSION SYSTEM," the entire disclosure of which is incorporated by reference in its entirety herein.

FIELD OF THE INVENTION

The present invention relates to surgical methods and assemblies employing the application of electrical energy to tissue to achieve a predetermined surgical effect, and, more particularly, to achieve such effect with reduced likelihood of inadvertent tissue damage and with better control of energy application to tissues.

BACKGROUND OF THE INVENTION

The potential uses and recognized advantages of employing electrical energy for surgical purposes are ever-increasing. In particular, for example, electrosurgery techniques are now being widely employed to provide significant localized control advantages in both open and laparoscopic, including arthroscopic, applications relative to prior traditional surgical approaches.

Electrosurgical techniques use an instrument with working surfaces that contact tissue, such as a tissue ablation or cutting device, a source of radio frequency (RF) electrical energy, and a return path device, commonly in the form of a return electrode pad. The working surfaces that contact the patient in the region where the surgical effect is to occur are commonly called the active electrode or electrodes. The return path device contacts the patient either directly on the tissue or indirectly through, for example, a conductive liquid such as blood or normal saline. The return path device provides a return electrical path from the patient's tissues. Both the instrument and the return path device are connected using electrically conductive wires to the source of the radio frequency electrical energy which serves as both the source and the sink for the electrical energy to produce a complete electrical circuit. When the instrument and the return path device are separate devices the technique is termed monopolar. In some cases the instrument contains working surfaces that both supply the electrical energy and provide the return path. In these cases the technique is termed bipolar.

FIG. 3 illustrates a schematic of an electrosurgical system generally of the above-described type which includes an electrosurgical generator 1 with the generator electronics 2 (including the radio frequency (RF) electrical energy source, controls, and power supply being included in the electronics), as well as an electrosurgical accessory or instrument 100 and a return system 110 which is mechanically separated from the accessory 100. As such, the configuration of FIG. 3 is of the monopolar type. An output connector plug 3 and a return connector plug 4 of the accessory 100 connect to the output connector 5 and the return connector 6 that are part of the generator 1. The output connector plug 3 and a return connector plug 4 typically are molded plastic parts with metallic prongs (not shown) or receptacles (not shown). One or more of the metallic prongs in the output connector plug 3 connect to the output line 7 of the accessory 100, which typically consists of one or more conductive metal wires covered with an insulating coating. The output line 7 passes from the distal end of the output connector plug 3 and has a length suited to have the handle 8 of the accessory 100 a comfortable distance from the generator 1. The output line 7 passes into the proximal end of the accessory handle 8. The output line 7 is routed through the accessory handle 8 and may connect to a variety of internal conductors (not shown) that eventually make electrical contact with the active element 9 of the accessory 100, such as a blade. The accessory active element 9 may be in either direct or indirect contact with the patient 10. Electrosurgical energy passes from the active element 9 to the patient 10. The electrical return path is provided by the return system 110, which again is separate from the accessory 100 in the illustrated monopolar configuration of FIG. 3. The return system 110 consists of the return line 11 which typically connects with one or more metallic receptacles (not shown) that are molded into the housing of the return connector plug 4 and that, in turn, connect to the return connector 6 that is part of the generator 1. The return line 11 typically consists of one or more conductive metal wires covered with an insulated coating. The return line 11 exits the distal end of the return connector plug 4 and connects to the return path device 12 of the return system 110, which is usually a return electrode pad when monopolar procedures are used and as contemplated by the configuration of FIG. 3.

A variation of the accessory 100 from FIG. 3 is presented in FIG. 4 in the form of a schematic of an electrosurgical accessory 100'. In this case a supplemental return line 13 of the return system 110' extends from the return connector plug 4 to the output connector plug 3 where it interfaces with the return line 11. The supplemental return line 13 will be long enough to span the distance between the output connector 5 and the return connector 6 and allow the user enough slack to conveniently connect the output connector plug 3 and the return connector plug 4 to the generator 1. This length will typically be between 6 and 18 inches. The length should not be longer than necessary to avoid producing confusing clutter.

The output line 7 and the return line 11 may leave the output plug 3 separately or joined together in a cable in the case of either of the configurations presented in FIGS. 3–4. Although this is appropriate for the monopolar configurations presented in FIGS. 3–4, joining the lines together is particularly advantageous when they both go to an accessory which is of the bipolar type, and one embodiment of which is schematically presented in FIG. 5. In this case, the accessory handle 8 of the accessory 150 provides electrical continuity from both the output line 7 and the return line 11 to the active element 9 and the return path device 12 (e.g., return electrode), respectively. In bipolar accessories in general, the active element 9 and the return path device 12 are often joined together mechanically, but not electrically, using an accessory electrode housing 14. The accessory electrode housing 14 can be of many forms, of which an insulated shaft is an example. The common feature of the various forms of the accessory electrode housing 14 is that it allows both the active element 9 and the return path device 12 to contact simultaneously the patient 10. Such contact may be either direct or indirect.

One embodiment of a prior art bipolar configuration is more particularly illustrated in FIG. 15, which is used in conductive liquid environments. The accessory 200 operatively interfaces with an electrosurgical generator (not shown) via an output connector 5 on the generator and a return connector 6 on the generator. The accessory 200 has a supplemental return line 13 passing from the return connector 4 to the output connector 3. The accessory 200 illustrated in FIG. 15 is a bipolar electrosurgical accessory that uses a return electrode and it will be compared to later figures to illustrate distinctive features of the subject invention. The device 200 illustrated in FIG. 15 includes a probe assembly 27 that has a probe handle 28 and a probe shaft 29. The output line 7 and the return line 11 are of a length needed to allow the surgeon to conveniently place the electrosurgical generator. The probe shaft 29 is coated with probe shaft insulation 30 that extends almost the complete length of the probe shaft 29. The probe shaft 29 is typically made of either a polymer, which may be flexible, or, more commonly, of metal. One or more channels (not shown) may pass through the probe shaft 29 to allow irrigation solution, aspirated materials, tools, light sources, or visualization equipment to pass into the patient. At the distal tip of the probe shaft 29 is the active electrode assembly 31 which includes the active electrode 32. The output line 7 may continue through the length of the probe assembly 27 and electrically connect to the active electrode 32. If the output line 7 does not directly connect to the active electrode, then one or more conductive elements (not shown) form a conductive path to the active electrode 32. The probe shaft 29 is electrically connected to the return line 11. A section of the probe shaft 29 is left uninsulated to be the return electrode 33. The illustrated device shows a probe shaft 29 made only from metal. If a polymeric or other insulating material forms the probe shaft 29, then the shaft 29 is not insulated and a conductive metal element is attached to form the return electrode 33. The active electrode assembly 31 is insulated from the return electrode 33 by an active electrode standoff insulator 34.

The return electrode 33 is a conductor that contacts whatever liquid (not shown) may be surrounding it. A perforated shield (not shown) may surround the return electrode 33 as well, but the shield allows conductive liquid to contact the return electrode 33. The conductive liquid needs to contact the return electrode 33 to form an electrically conductive path.

The probe shaft insulation 30 is selected to insulate the probe shaft 29 from contacting patient tissues that may lead to inadvertent electrical return paths. The insulation 30 is not selected to allow energy transfer by electrical fields to the probe shaft 29, and such energy transfer is not required, nor can it occur, when the return electrode 33 has electrical continuity with surrounding conductive liquid to generate a current return path.

The waveforms produced by the radio frequency electrical source in an electrosurgical procedure are designed to produce a predetermined effect such as tissue ablation or coagulation when the energy is conveyed to the patient's tissue. The characteristics of the energy applied to the tissue, such as frequency and voltage, are selected to help achieve the desired tissue effect.

Electrosurgical procedures can experience inadvertent problems that lead to unintended tissue damage. During electrosurgical procedures the depth of the effect to the tissue depends upon tissue properties, which change during the application of energy. It is desirable to not have the tissue effects change so rapidly that the surgeon has difficulty controlling the surgical result. During some procedures, such as minimally invasive surgical (MIS) procedures wherein surgical instruments are passed through small openings in the patient's tissue, energy can enter a patient's tissue at a location other than where the active electrode is positioned. Such inadvertent energy application can lead to burns or other complications. When surgical instruments are being inserted or withdrawn from patients during MIS procedures, concern exists for inadvertent activation of the RF energy source and tissue damage that could occur from such an event. One aspect of this problem occurs when the return path device is positioned such that it causes high current flux through tissue adjacent to it. High current flux can cause tissue burns or other damage. It would be desirable for the devices used by surgeons to not allow such inadvertent high current fluxes to occur.

The source of RF energy (the generator) has an output power that depends upon the operating characteristics of its design, including the design of its internal circuitry. Typically the generator is set by the clinical user to a setting that represents the output power desired. When the generator operates, the output power typically depends upon the impedance of the load into which the generator is delivering power. In general, the various generators available operate in modes that approximate constant voltage devices, constant power devices, or some hybrid mode that lies between constant voltage and constant current. The modes approximate constant voltage or constant power output due to the variations inherent in electronic component performance. Modem general purpose generators commonly used in operating rooms typically operate in a constant power mode when power outputs other than low power are desired.

Generator supply companies have long recognized the desirability of using constant power for major surgical procedures such as open surgical procedures. Consequently, the modem generators in operating rooms use a constant power mode. Recently, procedures, such as arthroscopic surgical procedures (e.g., tissue ablation and capsular shrinkage), that benefit from using a constant voltage mode have become increasingly common and important. Special purpose generators have been developed for these constant voltage procedures. Surgical instruments connect to the constant voltage generator and the RF energy is conveyed to the working surfaces using conductors of various types.

Constant power can lead to runaway interactions between the RF energy and the tissue. During electrosurgical procedures the tissue impedance eventually increases as the tissue is affected by the energy imparted to it. In an attempt to continue delivering constant power, a constant power source will increase the output voltage to overcome the increased tissue impedance. This increased voltage will lead to continued changes in the tissue with corresponding increases in tissue impedance, which, in turn, cause the generator to increase the voltage further. The cycle of events usually occurs very rapidly, so rapidly that during some procedures it is beyond the user's ability to respond quickly and prevent undesired tissue effects such as charring or excessive tissue destruction.

Constant voltage automatically reduces the rate that energy is supplied to the tissue as the tissue impedance increases. When constant voltage is used, the current delivered to the tissue, and consequently the power delivered, decreases as tissue impedance increases. This inherent response can greatly reduce or eliminate runaway interactions between the tissue and the RF energy applied to it.

To date, the advantages of constant voltage cannot be easily obtained from constant power generators. It would be beneficial for users, when they so desire, to easily and economically be able to have constant power generators deliver constant voltage to a surgical site. In particular, it would be useful for users to achieve the benefits of constant voltage supply without needing to modify existing generators or attach special adapters to generators. In cases where single use, or limited use, disposable surgical accessories are used, it would be particularly beneficial if the accessory makes the conversion from constant power to constant voltage. For example, it would be beneficial if an arthroscopic instrument intended for ablating tissue could be plugged into a constant power generator and apply power that approximated constant voltage to the tissue.

To date, the primary means for delivering RF energy to tissue while employing constant voltage requires using a constant voltage generator. Constant voltage electrosurgical generator design is known art, such that described in U.S. Pat. No. 5,472,443. Constant voltage electrosurgical generators have outputs that are constant voltage and do not convert the output from a constant power generator to be constant voltage. U.S. Pat. No. 5,472,443 also presents a means for retrofitting selected generators to modify the output, however the circuit presented has considerable complexity and does not lend itself to use in disposable products. The U.S. Pat. No. 5,472,443 circuit is also intended for use with surgical instruments that cut using a sharp edge, rather than using electrosurgical energy to produce the cutting action. Other known electrosurgical generator art limits the current flow, such as described in U.S. Pat. Nos. 4,092,986, 5,267,997 and 5,318,563. The art described in these patents is incorporated into generators and does not convert the mode of a constant power generator into constant voltage. U.S. Pat. Nos. 4,114,623 and 5,891,095 describe current limiting means, as opposed to voltage limiting means. Electrosurgical systems may use temperature sensing to control the power applied to the tissue, such as described in U.S. Pat. No. 5,440,681.

SUMMARY OF THE INVENTION

The present invention generally relates a system/method for executing an electrosurgical procedure on a patient (e.g., cutting, coagulation, desiccation, fulguration, ablation, tissue shrinkage).

A first aspect of the present invention allows for limiting a maximum voltage which is applied to a patient during an electrosurgical procedure using an electrosurgical generator and an electrosurgical assembly which is separate from and interfaces with the generator. The electrosurgical generator and electrosurgical assembly are separate components and may be operatively interconnected at the desired time to affect the execution of desired electrosurgical procedure. One particularly desirable application of the subject first aspect is when the electrosurgical generator is of a constant power type configuration, or even more preferably when the electrosurgical generator is operating other than on a constant voltage basis. In this case, the electrosurgical assembly may include one or more relevant components to effectively allow the electrosurgical assembly to execute an at least substantially constant voltage electrosurgical procedure, or stated another way to allow the electrosurgical assembly to deliver voltage at least at substantially a constant magnitude to the patient. This is desirable for a number of reasons, including for reducing the potential for tissue damage.

The first aspect of the present invention is embodied in an electrosurgical assembly (e.g., an instrument or accessory) which interfaces with an electrosurgical generator. Components of the electrosurgical assembly of the subject first aspect include an output assembly which is at least operatively interconnectable with the generator and also which is operatively interconnected with an active electrosurgical element or electrode (e.g., one or more blades, hooks, balls, spatulas, loops, pins, wireforms, tubes, tubes with fluid passageways, members of forceps, graspers, scissors). Any such electrode may include one or more surfaces for interfacing with the patient, and each such surface may be either curved or flat. Power from the generator is provided to the active electrosurgical element through the output assembly of the electrosurgical assembly such that an interface between the active electrosurgical element and the patient (e.g., direct, indirect) may affect execution of the subject electrosurgical procedure. Typically the output assembly will include an output plug which detachably interconnects with an output connector on the generator, as well as an output or power line and/or one or more other appropriate electrical conductors which extend between the output plug and the active electrosurgical element.

Completion of the circuit between the patient and the electrosurgical generator is provided by a return path element which interfaces with the patient (e.g., tissue, one or more fluids and including conductive liquids), as well as a return assembly which is operatively interconnected with this return path element and further which is at least operatively interconnectable with the electrosurgical generator. Typically, the return assembly will include a return plug which detachably interconnects with a return connector on the generator, as well as a return line and/or one or more other appropriate electrical/energy transfer members which extend between the return plug and the return path element. In the case of the subject first aspect, a shunt circuit extends between and interconnects the output and return assemblies (e.g., between the output/power line and the return line).

Various refinements exist of the features noted in relation to the subject first aspect of the present invention. Further features may also be incorporated in the subject first aspect of present invention as well. These refinements and additional features may exist individually or in any combination. There are various ways in which the shunt circuit utilized by the subject first aspect may be characterized. Voltage regulation during a given electrosurgical procedure may be affected by the shunt circuit. Limitation of the maximum voltage transferred/applied to the patient from the interface with the electrosurgical assembly may also be provided by the shunt circuit. Yet another characterization is that a constant power electrosurgical generator may be used by the subject first aspect of the present invention to execute an at least substantially constant voltage electrosurgical procedure using the electrosurgical assembly in accordance with this first aspect of the present invention. In one embodiment where the assembly of the first aspect is used with a generator which delivers something other than a constant voltage output and including a constant power generator, a voltage variation of no more than about 15% is realized throughout the electrosurgical procedure by the inclusion of the shunt circuit in the electrosurgical assembly in accordance with the subject first aspect, particularly over/throughout a patient impedance range from about 500 ohms to about 2,000 ohms.

The active electrosurgical element and return path element of the subject first aspect may be integrated with the electrosurgical assembly in a manner which provides a monopolar configuration/technique, as well as in a manner which provides a bipolar configuration/technique. A monopolar configuration/technique exists when the return path element is a separate device from that which carries the active electrosurgical element, whereas a bipolar configuration/technique exists when the active electrosurgical element and the return path element are incorporated in the same structure (e.g., both being positioned on a probe or the like). Although what may be characterized as "conventional" return path elements may be utilized in relation to the subject first aspect of the present invention (e.g., a return electrode pad for a monopolar configuration, conventional electrical conductors such as a metal tube or shaft with insulation disposed about all but an end portion thereof, which then interfaces with the patient, for a bipolar configuration), in one embodiment the return path element of the first aspect for a bipolar application includes a return coupler having a first dielectric body or component (e.g., one or more dielectric materials, alone or in combination with one or more non-dielectric materials). This first dielectric body or component directly interfaces with the patient during execution of the electrosurgical procedure (e.g., via tissue contact, via body fluid(s) contact), and also interfaces with an appropriate conductor of the return coupler (e.g., a hollow shaft, a solid shaft with one or more channels extending therethrough, at least some of which may be electrically conductive) in such a manner that energy from the patient first transfers, using nonconductive means, across the first dielectric body and then to the conductor when proceeding back to the generator via the return assembly. Stated another way, the return coupler effectively defines or is at least part of a capacitor in the return path to the generator, such that the energy from the patient is at least initially returned to the generator via electrical fields versus conduction. After transferring across the first dielectric body, conventional conduction structure/techniques may be employed.

The patient effectively has an impedance load associated therewith which may then be characterized as a patient impedance load. In one embodiment of the first aspect, the shunt circuit is disposed in parallel with this patient impedance load. Various types of shunt circuits may be utilized, preferably by being disposed in the noted electrically parallel relation to the patient. A single electronic element may define the shunt circuit, such as a capacitor. Appropriate electrical leads could then be used to electrically interconnect the capacitor with the output and return assemblies of the electrosurgical assembly. However, the shunt circuit may also include one or more electronic elements, and these electronic elements may be passive, active, or some combination of one or more passive and one or more active electrical components. Appropriate electronic components or elements for the shunt circuit of the subject first aspect include capacitors, inductors, resistors, transistors, diodes, and integrated circuits.

Options exist regarding the physical location of the shunt circuit associated with the first aspect of the present invention. In one embodiment, the shunt circuit may be positioned other than in a user handle which may be utilized by the electrosurgical assembly. This not only reduces the potential for an increased temperature of the handle or incorporating an appropriate cooling system within any such handle to address the heat buildup which will be caused by the shunt circuit, but also allows the existing space within any such handle to be used for other purposes (e.g., for certain electronics, for other systems such as suction/irrigation systems) or to allow the handle to continue to be of a desired size for providing an appealing physical interface with a user of the electrosurgical assembly (e.g., a surgeon). Appropriate locations for the shunt circuit include within an output plug of the electrosurgical assembly which again would detachably interconnect with an output connector on the generator, within a return plug of the electrosurgical assembly which again would detachably interconnect with a return connector on the electrosurgical generator, between portions of an output and return line which extend from an output plug of the electrosurgical assembly and a handle of the assembly or which otherwise extend to such a handle, or within an adapter of sorts which may be an in-line connector between the electrosurgical assembly of the subject first aspect and the electrosurgical generator. Notwithstanding the above-noted benefits of not including the shunt circuit within a handle which may be utilized by the electrosurgical assembly of the first aspect, one or more fundamental advantages associated with the first aspect may still be realized by having the shunt circuit within the handle, and therefore such is within the scope of the first aspect of the present invention.

A second aspect of the present invention also relates to a bipolar configuration of an electrosurgical assembly which receives power from an electrosurgical generator for executing an electrosurgical procedure on a patient. Components of the electrosurgical assembly include an output assembly which is at least operatively interconnectable with the generator and which is operatively interconnected with an active electrosurgical element or electrode (e.g., one or more blades, hooks, balls, spatulas, loops, pins, wireforms, tubes, tubes with fluid passageways, members of forceps, graspers, and scissors). Each active electrosurgical element may include one or more surfaces for interfacing with the patient, and such may either be flat or curved. Power from the generator is provided to the active electrosurgical element through the output assembly such that an interface between the active electrosurgical element and the patient (e.g., direct, indirect) may affect a particular electrosurgical procedure. Typically the output assembly will include an output plug which electrically interfaces with an output connector on the generator, as well as an output or power line and/or one or more other appropriate electrical conductors which extend between the output plug and the active electrosurgical element.

Completion of the circuit between the patient and the electrosurgical generator is provided by a return path element which interfaces with the patient (e.g., tissue, one or more fluids and including various body fluids) and which is mechanically interconnected with the above-noted active electrosurgical element to define a bipolar configuration (e.g., on a common probe). Another portion of this "return" to the generator is provided by a return assembly which is operatively interconnected with this return path element and further which is at least operatively interconnectable with the electrosurgical generator. Typically the return assembly will include a return plug which electrically interfaces with a return connector on the generator, as well as a return line and/or one or more other appropriate electrical/energy transfer members which extend between the return plug and the return path element. In the case of the subject second aspect, the return path element includes a first dielectric body or component (e.g., one or more dielectric materials, alone or in combination with one or more non-dielectric materials) which directly interfaces with the patient.

Energy from the patient is at least initially transferred through the return path element via a field effect or via one or more electrical fields in the case of the subject second aspect of the present invention, which again is limited to a bipolar application (e.g., by having the active electrosurgical element and return path element mounted on a common probe or the like). Known bipolar devices instead use conduction in this instance. During most electrosurgical procedures, and including minimally invasive procedures and open surgical procedures, there will be a liquid interface between the patient and the first dielectric body associated with the subject second aspect. Any appropriate conductive liquid may be utilized for this interface, including saline, lactated Ringers solution, as well as a combination of saline and one or more bodily fluids of the patient such as blood and/or perspiration.

Various refinements exist of the features noted in relation to the subject second aspect of the present invention. Further features may also be incorporated in the subject second aspect of present invention as well. These refinements and additional features may exist individually or in any combination. The first dielectric component may include a combination of materials (e.g., one or more dielectric materials in powder form, combined with a polymer or adhesive). In any case, the first dielectric component may include a first material which is subject to number of characterizations. This first material has a dielectric product which is greater than about 2,000 in one embodiment, greater than about 4,000 in another embodiment, and greater than about 8,000 in yet another embodiment. "Dielectric product" as used herein means the dielectric constant of the first material, multiplied by the dielectric strength of the first material. Materials having a dielectric product in accordance with the foregoing include alumina, diamond, boron nitride, polyimide, polyester, parylene, barium titanate, titanium dioxide, Teflon, and polycarbonate.

Another characterization of the first material which is at least part of the first dielectric component is that it may have a dielectric constant which is greater than about 10 in one embodiment, which is greater than about 20 in another embodiment, and which is greater than about 50 in yet another embodiment. Materials having a dielectric constant in accordance with the foregoing include ceramics, alumina, titanium dioxide, barium nitrate, and combinations thereof. The first dielectric component of the subject second aspect may be further characterized in relation to its wall thickness. The first dielectric component may have a wall thickness which is less than about 0.25 inches in one embodiment, which is less than about 0.10 inches in another embodiment, and which is less than about 0.01 inches in yet another embodiment.

Barium titanate is currently the preferred material to be the primary dielectric material for the first dielectric component of the return path element in accordance with the subject second aspect. The first dielectric component is at least about 50 wt % barium titanate in one embodiment, and is at least about 90 wt % barium titanate in another embodiment. Suitable energy transfer characteristics across the first dielectric component are realized when formed from barium titanate in the above-noted amounts, and further when: 1) the first dielectric component has a surface area of no larger than about 1 $in^2$ in one embodiment, no smaller than about 0.2 $in^2$ in another embodiment, and a surface area no smaller than about 0.007 $in^2$ in yet another embodiment; and/or 2) when the first dielectric component is the form of a tube, which is any shaped material that has one or more openings into or through it, with a wall thickness of no more than about 0. 5 inches in one embodiment, no more than about 0.1 inches in another embodiment, and about 0.020 inches in yet another embodiment, and being at least about 0.005 inches thick.

The return path element as a whole, which includes the first dielectric component, is also subject to a number of characterizations. The impedance of the return path element is less than about 800 ohms in one embodiment, is less than about 500 ohms in another embodiment, is less than about 300 ohms in another embodiment, and is less than about 200 ohms in yet another embodiment. Another characterization of the return path element is its voltage strength. The return path element is able to withstand a voltage exceeding 1,000 volts peak to peak in one embodiment, a voltage exceeding 2,000 volts peak to peak in another embodiment, and exceeding 5,000 volts peak to peak in yet another embodiment.

One configuration which may be utilized for the subject second aspect is a probe with a handle attached thereto. The probe may be characterized as including first and second longitudinal segments. The active electrosurgical element may be part of the first longitudinal segment and the return path element may be part of the second longitudinal segment. In any case, the first dielectric component may be in the form of a layer or the like which is disposed about an electrically conductive return tube or shaft of the return coupler, which in turn may be electrically interconnected with the return assembly (e.g., a return line having a return plug disposed on an opposite end thereof which detachably engages with a return connector on the generator). Another option is to provide the first dielectric component itself with a tubular construction (i.e., separately formed), and to interface/interconnect the same with an electrically conductive return tube or shaft of the above-noted type by disposing the first dielectric component over an end portion of the electrically conductive tube/shaft.

Additional components may be utilized by the subject second aspect of the present invention. One such component is an inductor that may be disposed in series with the return path element. This inductor may be characterized as affecting an offset of the impedance which may be associated with the return path element. The shunt circuit noted above in relation to the first aspect of the present invention may also be utilized in the subject second aspect of the present invention as well.

Based upon the foregoing, it should be appreciated that one primary objective of the present invention may be characterized as providing a surgical method and assembly which employ electrical energy to achieve a desired surgical effect while using the disposable or electrosurgical assembly/accessory to alter the output mode of the generator and thus improve control of the energy application to reduce the opportunity for inadvertent tissue damage. To achieve this objective, a surgical method associated with the present invention may include the steps of using surgical instruments that contain one or more elements of predetermined types to influence the manner in which energy transfers and thereby alter how RF energy is applied to the tissue. In particular, at least certain aspects of the present invention can be used to effectively limit the maximum voltage applied to the tissue during the electrosurgical process to reduce the interactions with tissue that lead to the aforementioned shortcomings associated with using constant power RF energy.

The beneficial effects of reduced inadvertent tissue damage further manifest themselves when the return path device uses one or more electric fields to couple return energy flow from the tissue to the generator which itself is another aspect of the present invention. Such a return path device may be characterized as a return coupler as noted above. This return coupler may include a dielectric insulating material that completely insulates an inner conductive element (e.g., the dielectric insulating material may be part of a capacitor in which one capacitor electrode is defined by the inner conductive element, and in which the other electrode is defined by conductive liquid and/or bodily tissue). The inner conductive element is part of the conductive electrical path that extends to the generator. The inner conductive element is insulated from surrounding conductive liquids and the patient tissue by insulation and/or dielectric materials that surround the inner conductive element. The insulation prevents the inner conductive element from contacting the tissue, including both direct and indirect tissue contact via a conductive liquid (e.g., normal saline). The inner conductive element is surrounded by one or more insulating materials and the inner conductive element may be composed of one or more materials that are regarded as electrically conductive, such as any of copper, silver, or aluminum or an alloy of such a material. Another suitable material for the inner conductive element is stainless steel. The inner conductive element will commonly be a tube, in which case a power line for the active electrode may be directed through the hollow interior thereof so as to electrically isolate this power line from the inner conductive element. In any case, the inner conductive element will typically be electrically connected via a suitable means, such a wire connected at or near its proximal end which extends to a return plug (possibly via the output plug), and then to the return connection on the generator. The inner conductive element with its surrounding insulation will typically have a handle attached to it at the proximal end where the return wire exits. The return coupler is suited for use as the return path device with instruments having an active electrode and may be attached to the device to form a bipolar configuration. The distal tip of the instrument could be the location of the return coupler and is an example of a location where an active electrode assembly could also be located.

The dielectric insulating material for the noted return coupler preferably has a combination of thickness, dielectric constant, dielectric strength and area such that it withstands the electric field voltages without breaking down and has a low enough impedance to allow adequate energy flow. The exposed area of the surrounding insulation will also affect the impedance of the return coupler. When a properly insulated inner conductive element is partially or wholly submerged in a conductive liquid, an electric field forms that transfers energy. The energy transfer is significantly more efficient when the return coupler contacts conductive liquid than when it contacts tissue. Consequently, the impedance increases when the return coupler does not completely contact liquid, such as when it is contacting tissue as the device is withdrawn from a patient. If the energy source is a constant voltage source, then the total energy delivered decreases as the impedance increases. The result is a reduced possibility of inadvertent tissue damage. However, if the energy source is a constant power source and in the case of an increase of the impedance of the patient's tissue, higher voltages would be provided by the generator, and thereby increased power. Use of the shunt circuit discussed above in relation to the first aspect of the present invention, and which is also discussed in more detail below as well, may be utilized to in effect limit the maximum voltage output of the surgical instrument for these cases.

Proper insulating materials for the noted return coupler consist of one or more substances that, when applied to the inner conductive element, withstand the voltage across the insulation and lead to a low enough impedance for the area selected to be the return coupler. A combination of high dielectric constant and high dielectric strength is desired for the return coupler. The impedance of the return coupler increases with increasing insulation thickness and the ability to withstand voltage also increases with insulation thickness. Therefore, a tradeoff exists between having low impedance and having high voltage withstand strength. A high dielectric constant allows a material to have increased thickness while reducing the penalty of increasing impedance. A high dielectric strength material allows thinner insulation, which decreases impedance, while reducing the impact that thinner coatings have on decreased voltage withstand strength. The properties of dielectric constant and dielectric strength can be combined into one variable, the dielectric product (DP) as noted above and again where:

$$DP=(\text{dielectric constant})\times(\text{dielectric strength}).$$

Dielectric constant is a dimensionless quantity and dielectric strength is measured in Volts/mil, where mil=$\frac{1}{1000}$ of an inch. A material with a large DP will have a lower impedance at a given insulation thickness than a material with a lower DP will have. Therefore, large DPs are desirable for the substances used in the insulation coating the inner conductive element of a return coupler. DPs greater than 2,000 are preferred, and DPs greater than 4,000 and even 8,000 are even more preferred. Materials with large DPs include alumina, diamond and similar coatings, boron nitride, polyimide, polyester, parylene, barium titanate, titanium dioxide (including the Futile, anatase, and brookite forms), Teflon, polycarbonate, and inorganic and organic substances that are similar to these or that contain significant amounts (greater than about 30 percent) of these or similar materials.

To obtain the mixture of properties needed for manufacturing return couplers it is likely that materials with more than one DP will be used for the insulating material thereof. An example would be mixing a large DP material such as extremely fine (particles measured in microns) powders of barium titanate or titanium dioxide with binders, adhesives, or polymers such as epoxies, urethanes, or polyester. In some cases the large DP material could be blended into a polymer that is formed into tube, such as shrink tubing.

High dielectric constant materials are beneficial substances to use to make the insulating material for the return couplers. High dielectric constant materials have dielectric constants greater than about 10 [dimensionless]. Preferably, materials with dielectric constants greater than 20 or even 50 are used in conjunction with other substances, such as binders or adhesives. Examples of high dielectric constant materials include ceramics, and more particularly alumina, titanium dioxide (including rutile, anatase, and brookite forms), and barium titanate.

The insulating substance or substances for the noted return coupler may be applied using chemical or physical deposition means, such as chemically forming a layer, coating, wrapping, or vapor phase deposition. Shrink wrap tubing may be loaded with high dielectric materials. The insulating coating will beneficially be less than about 0.025 inches thick and even more beneficially if it is equal to less than about 0.010 or even 0.005 inches thick.

A separate component, such as a preformed hollow bead, made from one or more materials with a large DP may be used as well. For example, a hollow tube with a suitable length may be slipped over the end of the inner conductive element and placed in electrical contact with it using a gap-filling conductor such as a conductive liquid or solid. For example, a ceramic bead in the form of a tube made substantially from barium titanate could be slipped over a stainless steel tube and held in place by a layer of conductive epoxy or other adhesive that substantially fills the annular gap between the bead and the tube to define the noted return coupler.

The impedance of the noted return coupler is also preferably less than about 800 ohms, with values less than 500 ohms being more preferred. An impedance of 300 or even 200 ohms or less is even more preferred. The impedance of the noted return coupler will depend upon the frequency at which it operates. The generators that supply energy for electrosurgery typically operate in the range of about 10 kilohertz to about 3 megahertz. The most common operating range is about 100 kilohertz to 1 megahertz. These ranges are for the cut waveform frequency and for the coagulation and fulguration frequencies that are pulsed or otherwise modulated by the generator. The impedance of the noted return coupler can be greatly reduced by putting an inductor in series with it and selecting the inductor to have a value that is in series resonance with the return coupler. Including a compensating inductor that is at or about the value needed for series resonance with the return coupler will increase current flow at the design frequency. This enhanced current flow does not pass through the insulation surrounding the inner conductive element of the return coupler. As the impedance of the return coupler changes, such as by contacting tissue rather than a surrounding conductive liquid, the resonant frequency will move away from the design value and the energy flow rate will decrease. The value for the inductor that compensates for the return coupler will not necessarily be the same as an inductor sized to be in resonance with the capacitive effects that occur due to energy transfer to and from tissue or conductive liquids. The value of the return coupler is independent of the capacitive effects that occur during energy transfer to tissue. A further increase in performance will occur by reducing overall impedance at a design frequency if the inductor is selected to resonate with the combined capacitance from the energy transferred to tissue or conductive liquids and that of the return coupler.

To facilitate use of the noted return coupler, a device using a compensating inductor may include the inductor as a component in the accessory or surgical instrument and not as a part of the generator. By including the inductor in the accessory or instrument, such as a single use or limited reuse arthroscopic instrument, the user will not need to alter the generators that are already available. The inductor could go into the plug that connects power to the wire leading to the active electrode, into the plug that connects the generator's return to the wire leading from the return coupler, in the handle, or as part of the wire or cable that leads from the generator to the active electrode, the return coupler, or both.

The noted return coupler reduces energy transfer by increasing impedance when used with an RF energy supply that is at least approximately constant voltage. If it is used with a constant power source, then the generator will increase the voltage to overcome any increased impedance. As described earlier, many modern generators operate in a mode that approximates constant power, so it again would be desirable to supply easily at least approximately constant voltage from such devices in order for the benefits of using return couplers will be easily available to users of constant power generators.

The output from an electrosurgical generator typically has two ports. One output port is the power and the other is the return. These ports typically are jacks into which plugs connect with suitable mating metallic connectors to make electrical contacts. RF energy conductive paths that include wires and other elements that convey RF energy, such as capacitors, inductors, and transformers, provide paths from the ports to the electrosurgical accessory or instrument and return path device. The RF energy is conveyed via these paths to the patient, where tissues and tissue interactions produce the electrical load. As will be described in more detail later, placing one or more suitable electronic components between the output conductive path and the return conductive path and in parallel with the patient load will cause the output from a constant power electrosurgical generator to at least approximate constant voltage output. The electrical components form a shunt circuit between the power and return lines. The shunt circuit has one or more components in parallel with the patient load. As will be described in more detail below, the components of the shunt circuit can be selected to accommodate variations that occur in the patient load and generator design.

The metallic connector for the power line in the power plug connects to a wire in the power plug and this wire exits the distal end of the power plug and continues to the proximal end of an electrosurgical accessory. The proximal end of the electrosurgical accessory usually has a handle into which the power wire passes. From there it connects, either directly or indirectly via intermediate electrical conductors, to an active electrode. The active electrode is usually in the distal tip of the accessory. Active electrodes take on many forms such as blades, hooks, balls, spatulas, loops, pins, wireforms, tubes, tubes with fluid passages, and members of forceps, graspers, and scissors. Active electrodes may be one element of bipolar devices or they may be part of a monopolar configuration. The shunt circuit may be used in conjunction with all manner of active electrodes and their uses (i.e., may be used in any monopolar or bipolar configuration/application). Active electrodes may be used for cutting, coagulation, dessication, fulguration, ablation, tissue shrinkage, or other purposes for which electrosurgery is used in either monopolar or bipolar applications. In all cases, a continuous RF electrical energy path exists from the electrosurgical generator to the active electrode when energy is applied to the surgical site. The metallic connector for the return line in the return plug connects to a wire in the return plug and this wire exits the distal end of the return plug and continues to the proximal end of an electrosurgical accessory for bipolar devices or to a separate return path device when used for monopolar applications. In the case of bipolar devices, the proximal end of the electrosurgical accessory usually has a handle into which the return wire passes. From there it connects, either directly or indirectly via intermediate electrical conductors, to one or more return path devices, such as return electrodes or return couplers of the type contemplated by the second aspect of the present invention addressed above. Return electrodes in bipolar applications have one or more metallic or other electrically conductive elements that directly or indirectly contact patient tissues. Return electrodes provide an energy return path by providing an electrically conductive return path.

Direct contact with patient tissues occurs when the active electrode or return path element contacts patient tissues. Indirect contact with patient tissue occurs when an intermediate substance, such as conductive liquids, including solutions that contain blood or saline, conducts electrical energy for at least part of the energy flow path.

The variations in how the active electrode and return path device contact the tissue leads to variations in the load impedance. Similarly, changes caused by the application of electrosurgical energy, such as liquids boiling, tissue dessication or ablation, and electric spark formation also cause the load impedance to vary. Electrosurgical generators do not all have the same output frequency and the differences in output frequency also cause the load impedance to vary. As will be described later, one or more shunt circuits can be used to accommodate these variations.

The shunt circuit may be as simple as a single component, such as a suitably selected capacitor. The power output to the patient load with such a component much more closely approximates constant voltage than without it. As will be described later, reduced sensitivity to generator frequency and other variables can be achieved by including additional passive electronic elements such as inductors, resistors, and additional capacitors. Besides passive elements, active elements such as transistors, diodes, and integrated circuits may be used.

The shunt circuit may be included in the accessory device or the plugs or wires associated with it. For example, the wire from the return plug can be routed to the power plug and the shunt circuit can be incorporated into the power plug. This approach allows the power wire and the return wire to both exit from the distal portion of the power plug as part of a single cable, a feature that can be particularly beneficial for bipolar applications where both wires need to be routed to the accessory. Analogously, the shunt circuit may be in the return plug if the power wire and any control wires are routed to the return plug. Incorporating the shunt circuit into the power plug, compared to placing the components in the handle, prevents any increase in size from inconveniencing the user because of adding the shunt circuit. Similarly, placing the shunt circuit components in the plug will keep any heat that they may generate from heating the accessory handle and allow the plug to be designed with suitable heat sinks such as air flow holes or heat sinks such as extended surface features. The plug is also away from bodily fluids and solutions such as normal saline that may tend to penetrate and compromise circuit elements unless special precautions are taken. Such precautions typically add size and weight to accessories and, consequently, are not desirable in components being held and manipulated by surgeons. If the shunt circuit is placed in the handle, fluid flows through the handle, such as for aspiration or irrigation, may be used to cool components.

The shunt circuit may be placed in locations other than one of the plugs. The shunt circuit may also be placed along the cable between the plugs and the accessory. If it is desired, the shunt circuit may also be incorporated into a module that plugs into the power output and return jacks of an electrosurgical generator. The module would have one or more output ports that connect to connectors for the accessory, return path device, or both. Such a module may be reusable or a single use device. Similarly, the accessory and return path device may be reusable or single use devices.

Constant voltage operation provides benefits other than helping the noted return coupler to reduce inadvertent tissue damage. More controlled application of electrosurgical energy to tissue exists during both open and MIS procedures. For example, smoke and eschar accumulation are problems during both open and laparoscopic procedures. Eschar is the accumulated tissue thermal decomposition products that accumulate on electrosurgical instruments. Smoke production and eschar accumulation are reduced when using approximately constant voltage compared to using approximately constant power, such as during monopolar cutting using blades made from high thermal conductivity metals (metals with thermal conductivities greater than that of stainless steel) that have been insulated to control the application of electrosurgical energy (both thermal and electrical energy) to the active regions where the desired surgical effect (such as cutting) is desired. In this case the required voltage and power is lower than occurs when using blades that do not restrict how much electrosurgical energy is applied to regions other than the active regions. Similarly, arthroscopic ablation procedures produce less tissue charring and more controlled tissue removal occurs when the electrosurgical energy used at least approximates constant voltage compared to constant power.

When electrosurgical energy is applied to the surgical site, an RF energy path exists between the power port, through conductive and other elements that carry RF power, through direct or indirect tissue contact, through tissue, and the return port. As is obvious to one skilled in the electrosurgical art, the descriptions for power port and return port connections can be interchanged in that the RF energy is alternating.

The power port may be the monopolar output and the return port may be the monopolar return port. Using the monopolar ports is desirable for use with some bipolar applications where high power or high voltages are desired, such as during arthroscopic ablation. For example, arthroscopic ablation using a general purpose electrosurgical generator can be facilitated using the coagulation, dessication, or fulgurate mode because the high peak to peak voltages promote arc formation. Using these high voltage modes can lead to unintended tissue damage with a constant power output. Using a mode that approximates constant voltage reduces the possibility of unintended tissue damage.

In other cases, the power and return ports may be bipolar outputs. These ports may be selected when lower power outputs are desired, such as for neurosurgery or when collagen shrinkage is desired. Collagen shrinkage procedures may include arthroscopic or cosmetic surgery.

Special features may exist in the port connections on the electrosurgical generator. A common feature on electrosurgical generators is for one or more control wires to extend from the accessory to the power plug and from there to one or more additional connectors and jacks in the generator. These control wires connect to one or more switches in the accessory, typically in the handle, and allow the user to activate the generator and have it deliver power. Another common feature is for the return path device in the form of a monopolar return electrode pad to have two wires leading from it to the return plug and for the return plug to connect to a jack having two conductive contacts. The two conductive paths are used to implement features that measure the contact impedance between the return pad and the patient's skin to determine whether adequate contact exists to avoid unintentional burns where the return pad is applied to the skin. These additional conductive paths may be routed so that they pass through a single plug, such as the power plug, to reduce the number of cables leading to an accessory, such as a bipolar device.

DETAILED DESCRIPTION

The present invention will now be described in relation to the accompanying drawings which at least assist in illustrating its various pertinent features. This description starts with the output mode conversion circuit that converts the output from a constant power electrosurgical generator to approximately constant voltage. The description then covers the return coupler. The final description covers the output mode conversion circuit in conjunction with the return coupler.

Figure 1:
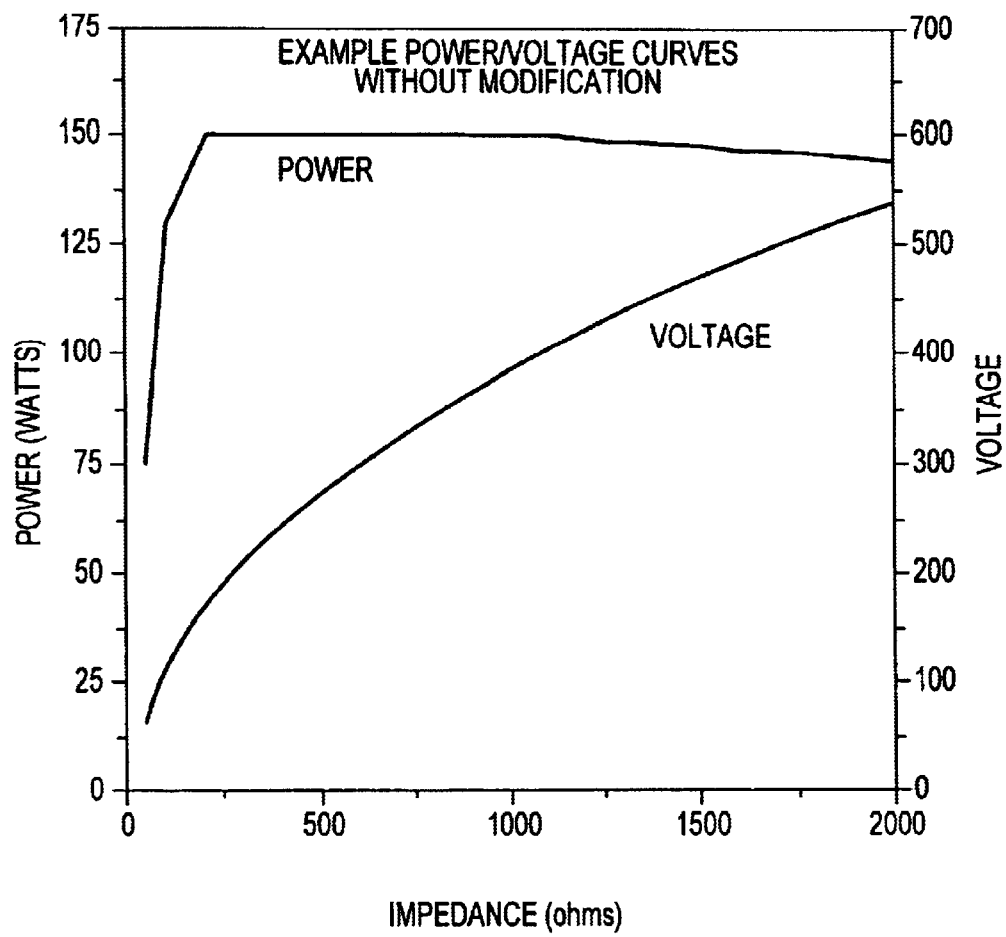
FIG. 1 portrays an example power and voltage output from a constant power electrosurgical generator.

FIG. 1 illustrates the power and voltage outputs from a modern electrosurgical generator that produces approximately constant power. As the load impedance increases, the voltage produced increases. The power shown is the average power in watts and the voltage shown is RMS voltage. Test measurements indicate what impedances are expected. Typical patient load impedances during, for example, arthroscopic ablation, are about 1,700 ohms and range during use from about 1,000 to about 4,500 ohms. The voltage needed to sustain the arc during such a procedure is between about 200 and 400 RMS volts, although using an RF energy source that produces pulses that have considerably higher voltage help start the arc and using a coagulation, dessicate, or fulgurate mode is usually beneficial. During open surgical cutting procedures using standard stainless steel blades, the typical impedances are about 1,000 to 4,000 ohms and the voltage needed during cutting is about 200–300 RMS volts. The impedances stay about the same, but the required voltages can decrease to less than 100 RMS volts when using special blade designs that use high conductivity materials (materials with thermal conductivities at least greater than that of 304 stainless steel) and that are insulated to control the application of electrosurgical energy to the active regions where energy application produces the desired surgical effect.

Figure 2:
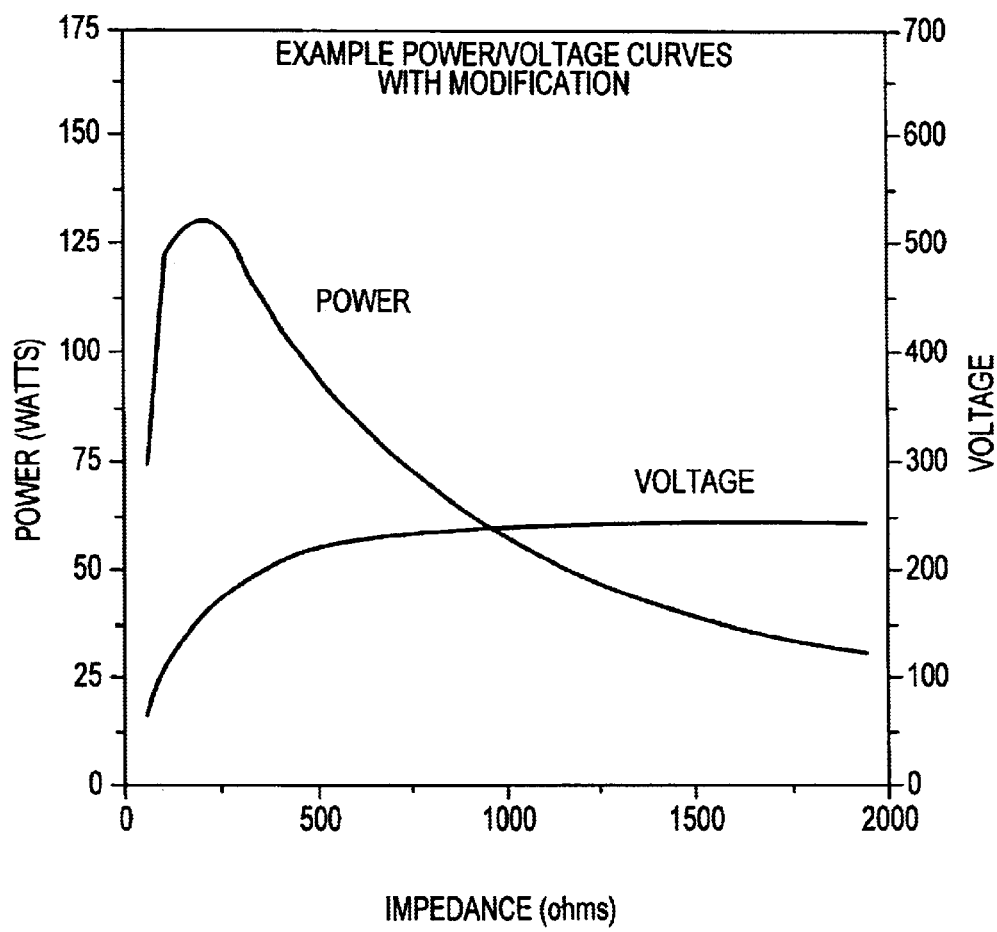
FIG. 2 portrays an example power and voltage output from a constant power electrosurgical generator after conversion to approximately constant voltage using a shunt circuit of an electrosurgical accessory or assembly in accordance with one or more aspects of the present invention.
Figure 3:
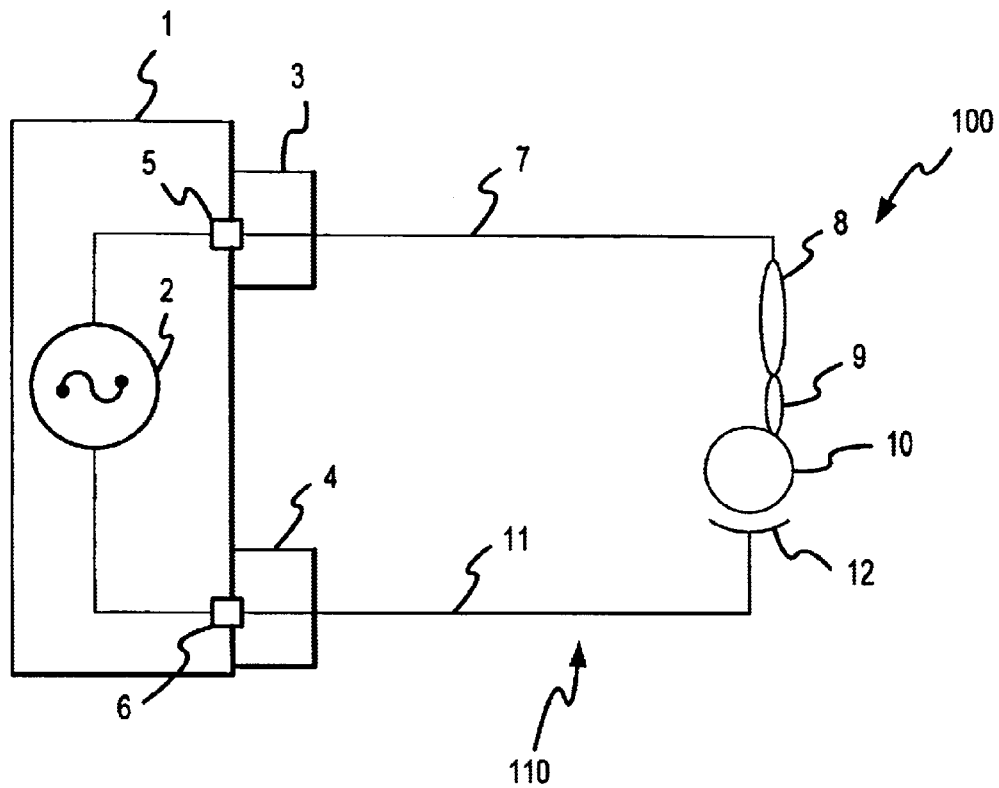
FIG. 3 schematically portrays a prior art setup of an electrosurgical generator and its application with a patient in a monopolar configuration.
Figure 4:
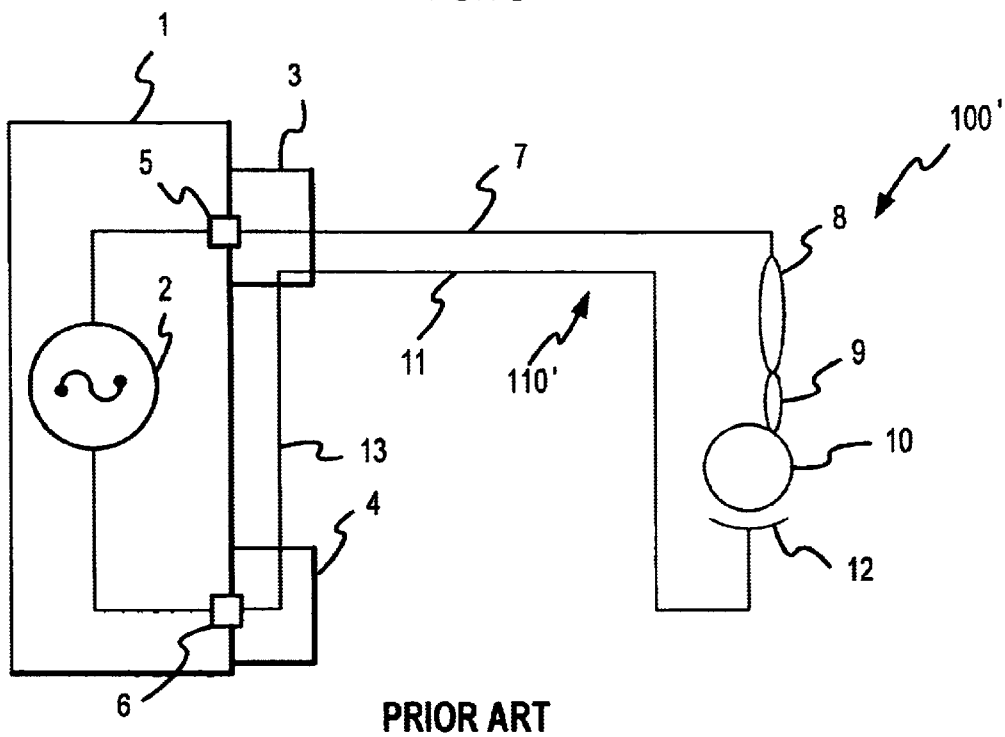
FIG. 4 schematically portrays a prior art modification of the setup presented in FIG. 3 in which the return line is routed through the power plug.

FIG. 2 illustrates the power and voltage applied to tissue after employing a shunt circuit in accordance with one or more principles of the present invention which are addressed in more detail below. FIG. 2 illustrates that a shunt circuit can produce approximately a constant voltage that is applied to the tissue over the range of tissue impedances of most interest. This range is about 500 to 2,000 ohms, although it can extend up to 3,000 or 4,000 ohms for momentary excursions. The typical operating conditions are in the range of about 1,000 to 2,000 ohms.

Figure 6A:
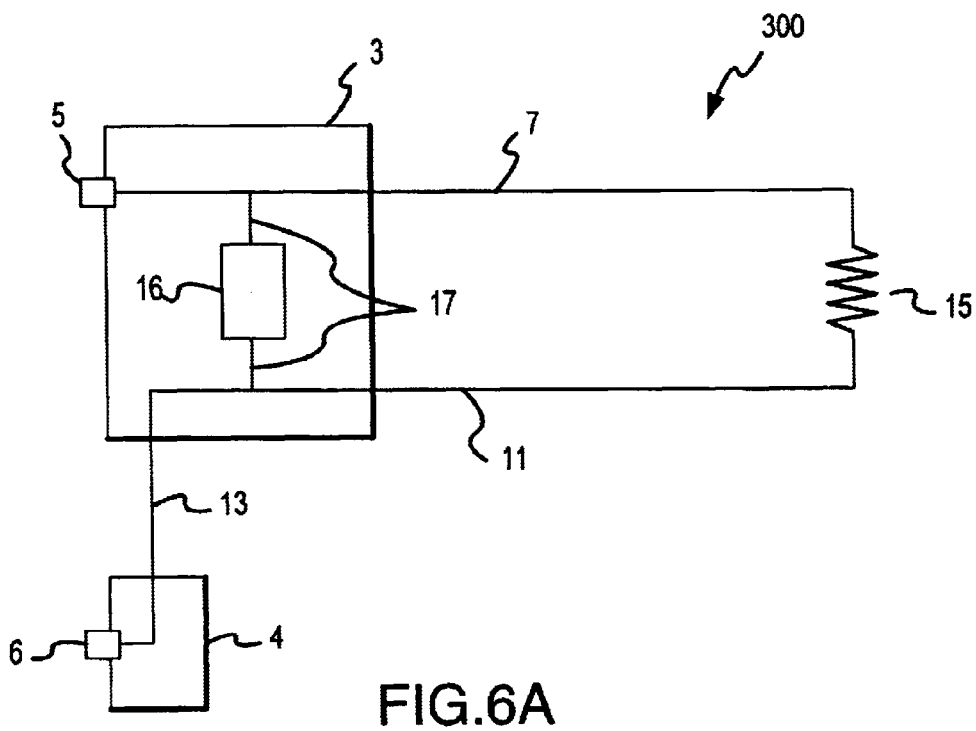
FIG. 6A portrays a shunt circuit located within the power plug of an electrosurgical accessory in accordance with one or more principles of the present invention.

Various configurations/arrangements of electrosurgical assemblies for interfacing with an electrosurgical generator 1 for executing an electrosurgical procedure in accordance with one or more principles of the present invention will now be addressed. Individual components of electrosurgical systems which have already been addressed herein and which may also be utilized by the present invention will continue to be similarly identified using the same reference numeral. FIG. 6A illustrates a shunt circuit 16 located within the output connector plug 3 of an electrosurgical assembly 300. Only those portions of the electrosurgical assembly 300which effectively define the electric circuit between the generator and the patient 10 are illustrated. The shunt circuit 16 consists of one or more electronic components (not shown). The electronic components may be any suitable combination of one or more passive components (capacitors, inductors, resistors) one or more active components (all electronic components that are not active, including diodes, transistors, and integrated circuits, such as voltage regulators), or both. Example shunt circuits are described in more detail later. Shunt circuit leads 17 connect the shunt circuit 16 to the output line 7 and the return line 11 where these lines pass through the housing of the output connector plug 3. The shunt circuit 16 may be used with any configuration of an electrosurgical assembly which interfaces with a generator to execute an electrosurgical procedure, including those discussed above in the Background of the Invention.

The electrical load of the patient 10 interacting with the electrosurgical energy provided by the electrosurgical assembly 300 is represented by the patient load 15 in FIG. 6A. The patient load 15 will typically be a complex impedance with both a resistance, $R_p$, and a reactance, $X_p$. As will be appreciated by those skilled in the art, $R_p$ and $X_p$ will together from the impedance, $Z_p=R_p+jX_p$, of the patient load 15. "j" is the square root of −1. Similarly, the shunt circuit 16 will have an impedance, $Z_s=R_s+jX_s$.

Figure 6B:
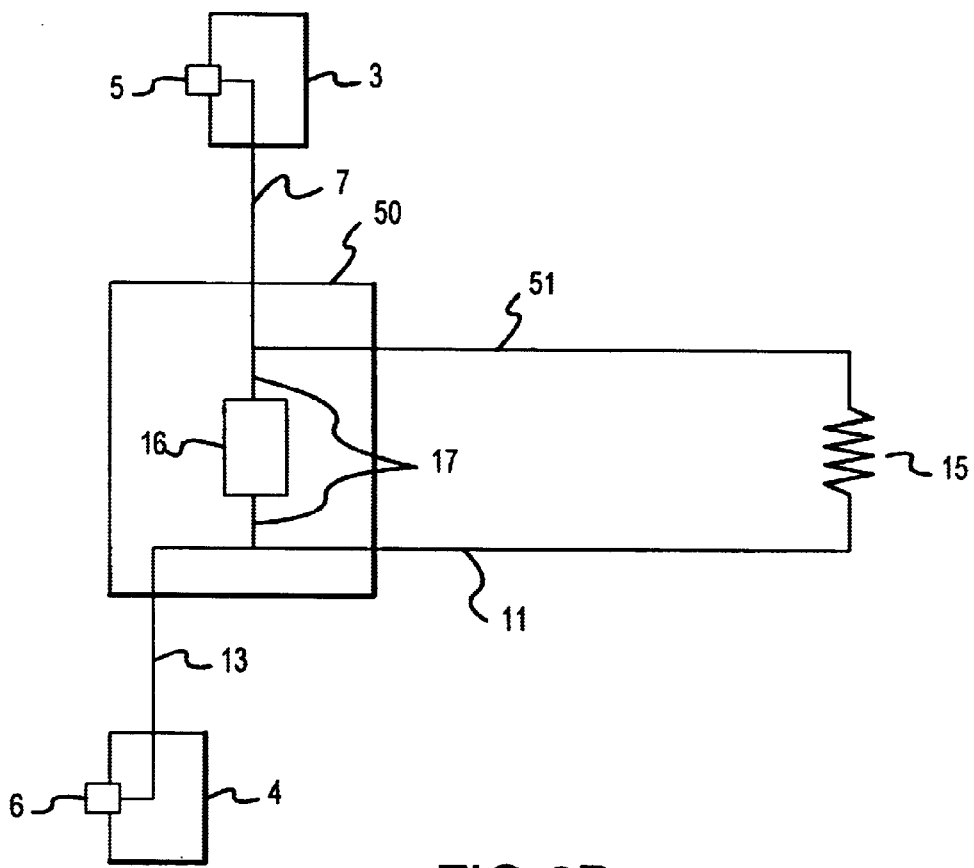
FIG. 6B portrays an alternative location for the shunt circuit of FIG. 6A.

FIG. 6B illustrates an alternative location of the shunt circuit 16 in which it is included in a shunt circuit module 50 that is separate from both the output connector plug 3 and the return connector plug 4. Extending from the shunt circuit module are the power line 51 and the return line 11. These lines go to the electrosurgical accessory (not shown) and supply power to the patient load 15.

Figure 6C:
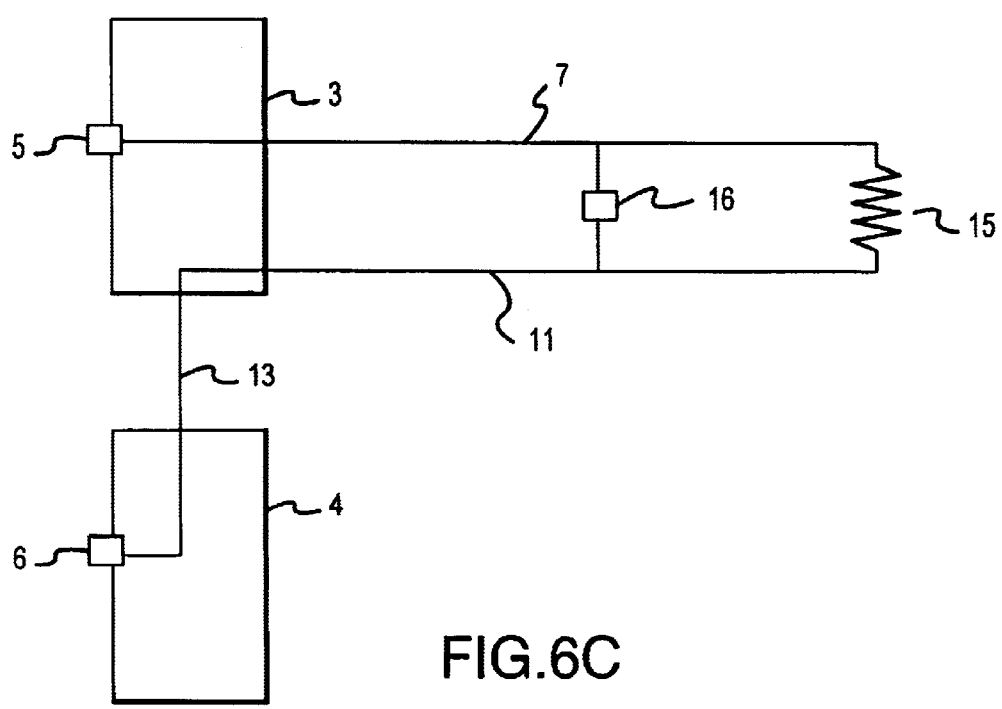
FIG. 6C portrays an alternative location for the shunt circuit of FIG. 6A.

FIG. 6C illustrates an alternative location of the shunt circuit 16 in which it is included in a cable consisting of the output line 7 and the return line 11, and possibly other lines (not shown) that may be used for a variety of purposes, such as control. The shunt circuit 16 may be in a container (not shown) that may be hard or soft or it may be surrounded by a casing including one or more flexible or rigid elements.

Figure 5:
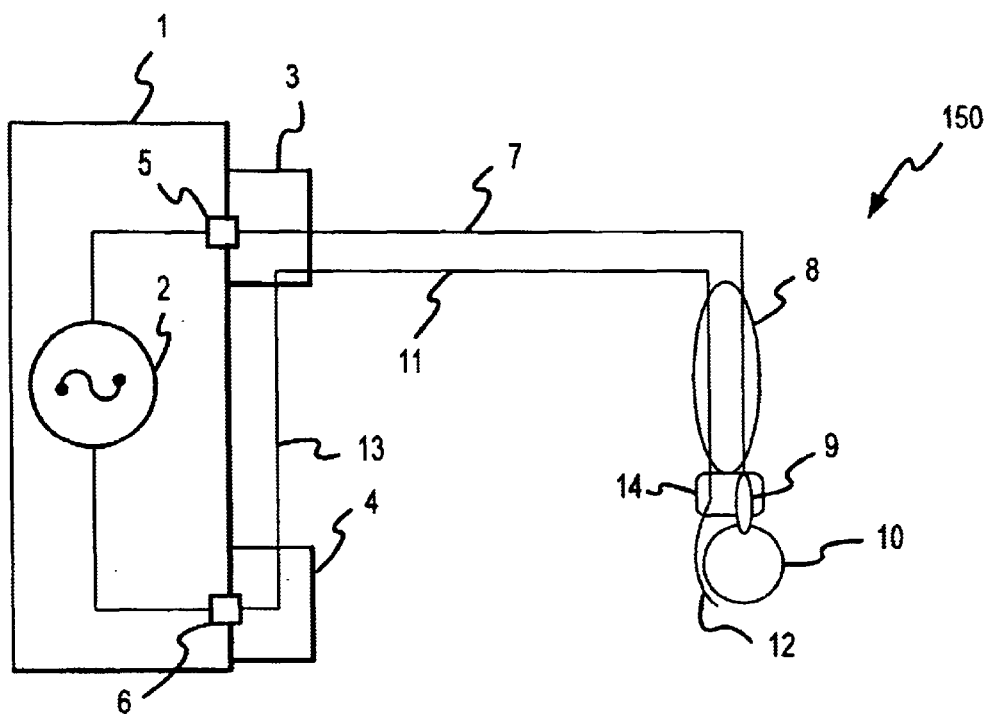
FIG. 5 schematically portrays a prior art setup of an electrosurgical generator in which the return line is routed through the power plug and in which the active and return electrode are combined into a bipolar accessory configuration.
Figure 6D:
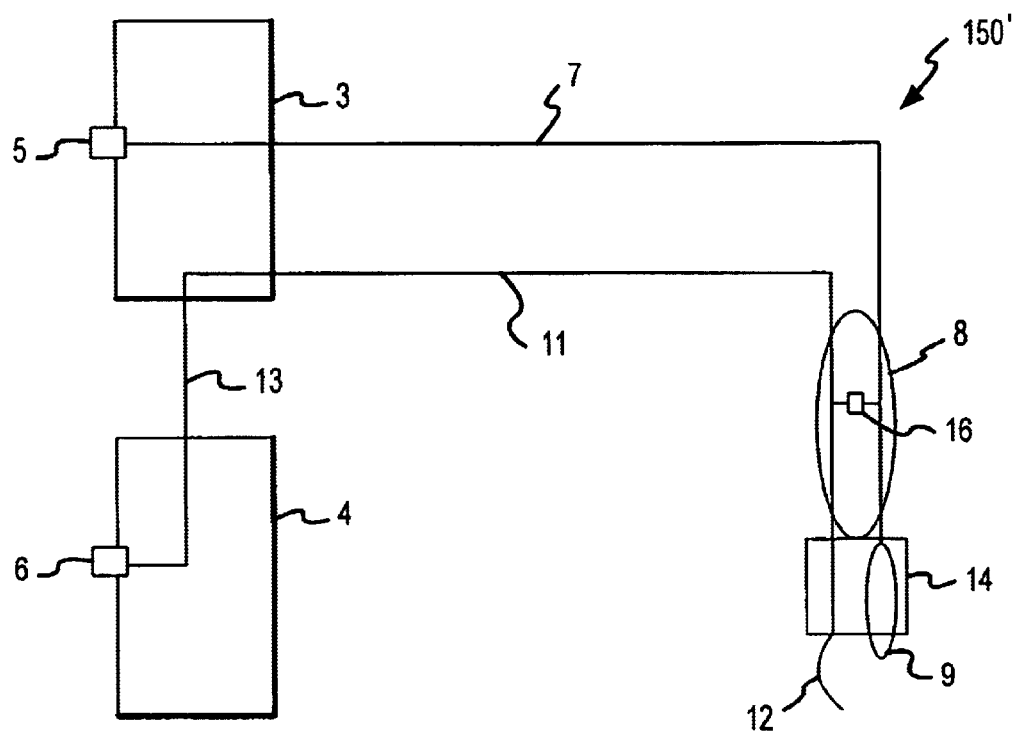
FIG. 6D portrays an alternative location for the shunt circuit of FIG. 6A.

FIG. 6D illustrates an alternative location of the shunt circuit 16 in which it is included in the physical structure of an electrosurgical accessory 150' generally of the type presented in FIG. 5, and in this illustration in the handle 8.

Figure 7:
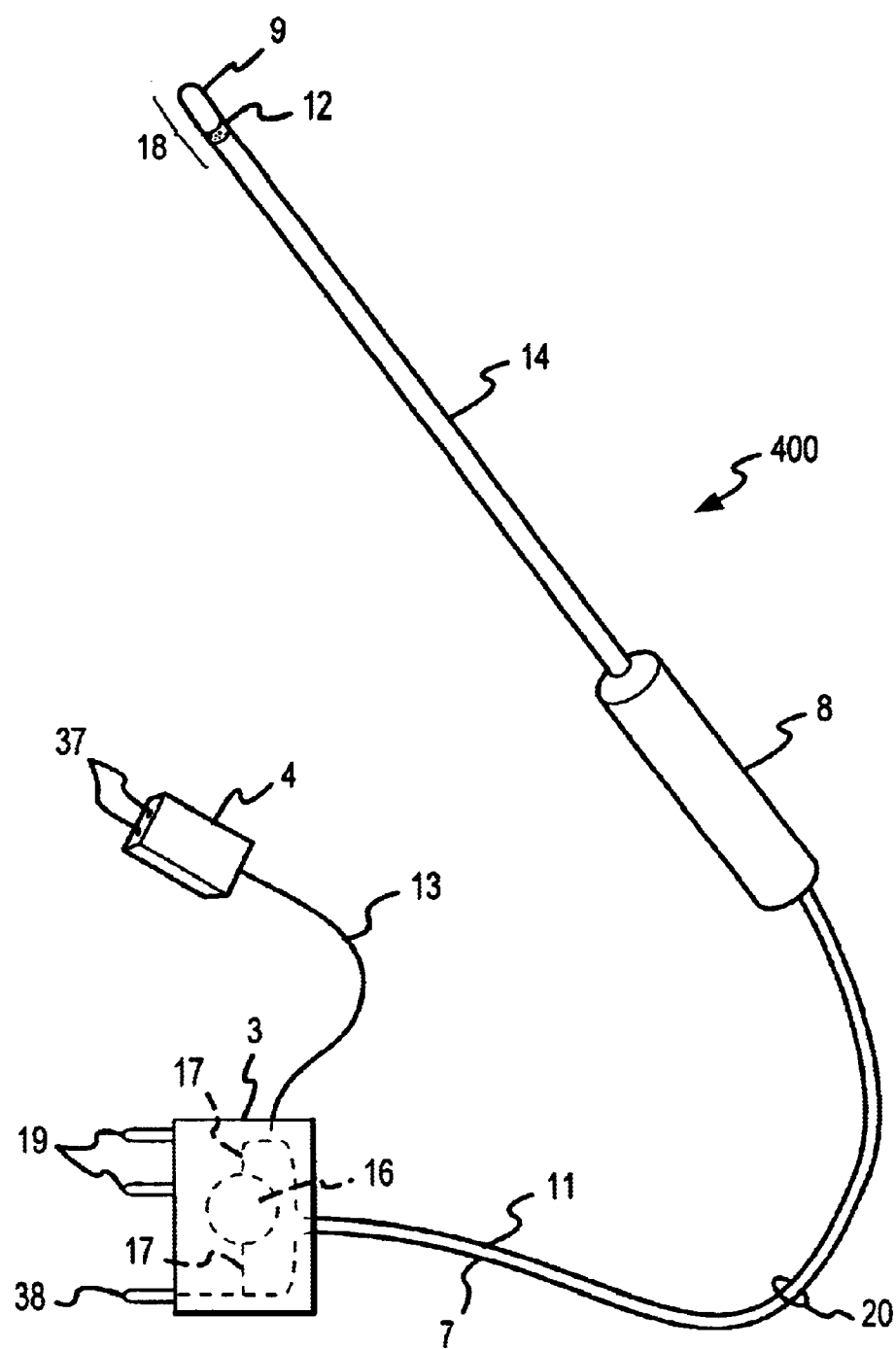
FIG. 7 illustrates one embodiment of an electrosurgical accessory which incorporates the shunt circuit of FIG. 6A and which is in accordance with one or more principles of the present invention.

FIG. 7 illustrates the use of the shunt circuit 16 from FIG. 6A in a particular electrosurgical assembly 400 of the bipolar type. Output connector plug 3 and return connector plug 4 are joined by supplemental return line 13. Return connector plug 4 has internal return conductors 37 molded into it to connect with the previously shown return connector 6 that is part of the generator 1. The internal return conductors 37 connect to the supplemental return line 13. Supplemental return line 13 passes into output connecter plug 3. Supplemental return line 13 transitions into return line 11.

Output connector plug 3 has three pins 19 and 38, as is typical for electrosurgical accessories that are manually activated from the handle. The cut and coagulation control pins 19 connect to control wires (not shown) that run up to the accessory handle 8 where they connect to suitable switches (not shown). Output power pin 38 connects to the previously shown output connector 5 that is part of generator 1. Output line 7 is electrically connected to output power pin 38. Shunt circuit 16 is connected to output line 7 and return line 11 using shunt circuit leads 17. These leads and the components of the shunt circuit 16 may be part of a circuit board or other means for making a subassembly that is incorporated into the device.

Output connector plug 3 may be whatever shape or design is appropriate to enclose and protect the parts that it contains. Possible implementations include overmolding, joining housing parts using ultrasonic welding or adhesives or mechanical fasteners such as screws. The design may include features to cool electronic components. These features may include holes or fins to promote air flow. The design may be made in whole or part from metal or other substance or substances that promote heat transfer. The preferred embodiment is to mold housings with suitable spaces to hold the components after they have been fabricated into subassemblies. Sliding penetrating connectors of types familiar to those skilled in the art may then be used to make connections.

The output line 7 and the return line 11 exit the output connector plug 3 along with any control lines (not shown) as a joined common cable assembly (portrayed by 20) and enter the accessory handle 8. The output line 7 passes through the handle 8 and accessory electrode housing 14 (shown here as a shaft) and is electrically connected to the accessory active element 9. The return line 11 passes through the handle 8 and the accessory electrode housing 14 and is electrically connected to the return path device 12.

The electrode housing 14 may be either flexible or rigid, or some combination of flexible and rigid elements, depending upon the clinical requirements for a particular embodiment. As will be shown later, the electrode housing 14 is often a metal shaft that is covered with insulation.

Figure 8:
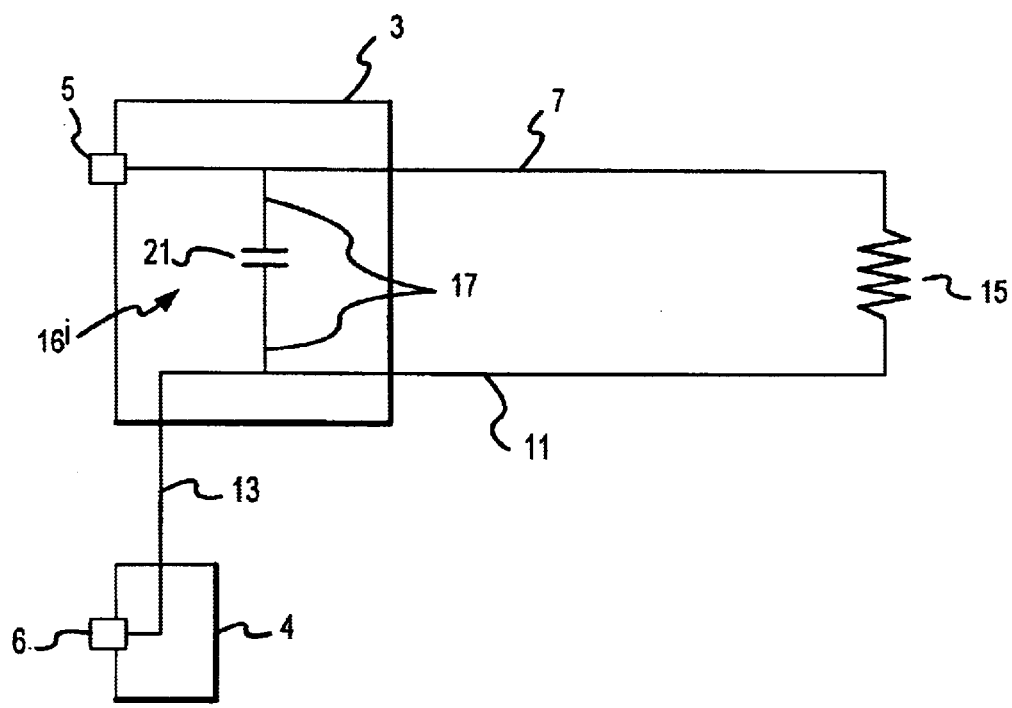
FIG. 8 schematically illustrates the use of a capacitor for use in the shunt circuit of FIGS. 6A–D.

FIG. 8 illustrates one embodiment (e.g., a layout of particular electronic components) which may be utilized by the shunt circuit 16 of FIGS. 6A–D, but which is illustrated only in relation to FIG. 6A for convenience. The shunt circuit $16^i$ of FIG. 8 consists of a single capacitor 21. The capacitance used depends upon the output frequency of the generator 1 used and the design impedance of the patient load 15. When the output frequency is between about 200 kilohertz and 800 kilohertz a capacitance of about 0.47 nanoFarads has been found to provide reasonable performance. The capacitors used need to withstand the output voltage of the generators for which the device is to be used.

A general approach for determining a shunt circuit design follows. The shunt impedance is a complex quantity with a resistance, $R_s$, and a reactance $X_s$. Using the subscript s to denote the shunt impedance as $Z_s$ and the letter j to denote the square root of −1 the following expression exists.

$$Z_s := R_s + jX_s \quad (1)$$

A similar expression exists for the patient load impedance $$Z_p := R_p + jX_p \quad (2)$$

Set up the total impedance by putting shunt and the patient load impedances in parallel $$Z_t := \frac{1}{\frac{1}{Z_s} + \frac{1}{Z_p}} \quad (3)$$

which is equal to $$Z_t = \frac{1}{\frac{1}{R_s + jX_s} + \frac{1}{R_p + jX_p}} \quad (4)$$

The RMS voltage, V, is the square root of the apparent power divided by the impedance magnitude. The generator "sees" apparent power as the load. The voltage across the patient load for a selected power output, shunt impedance, and patient load impedance is given by the established relationship between voltage, power and impedance as shown in equation 5:

$$V = \sqrt{\frac{P}{|Z|}} \quad (5)$$

For the purposes of designing with the subject invention, substitute $Z_t$ from (4) into (5) to obtain:

$$V = \sqrt{\frac{P}{\left|\frac{1}{R_s + jX_s} + \frac{1}{R_p + jX_p}\right|}} \quad (6)$$

Evaluating the magnitude of the denominator leads to equation 7.

$$V = \frac{P}{\sqrt{\left(\frac{R_s}{R_s^2 + X_s^2} + \frac{R_p}{R_p^2 + X_p^2}\right)^2 + \left(\frac{X_s}{R_s^2 + X_s^2} + \frac{X_p}{R_p^2 + X_p^2}\right)^2}} \quad (7)$$

Therefore, a specific voltage across the patient load occurs when a specific generator output power is selected and specific shunt and patient load impedances occur.

As conditions change at the surgical site, there can be many different patient loads. Designate two patient loads that form the lower and upper impedances for a design as $Z_1$ and $Z_2$. In accordance with equation 7 there will be two output voltages, $V_1$ and $V_2$ for any selected generator output power P. Two different patient impedances and, correspondingly, two different voltages will exist across the patient load. Therefore, if start at $Z_1$ and move to $Z_2$ then two output voltages, $V_1$ and $V_2$, will exist. The goal is to select $Z_t$ so that the variation between $V_1$ and $V_2$ meets a defined target. Set the target as the ratio $V_1/V_2 < K$, where $0 < K < 1$.

Using (7) to set up equations for $V_1$ and $V_2$, the voltages to be applied to patient tissue when the patient loads are $R_1 + jX_1$ and $R_2 + jX_2$ and then set up the ratio $V_1/V_2$ $$\frac{V_1}{V_2} = \frac{\sqrt{\frac{P}{\left|\frac{1}{R_s + jX_s} + \frac{1}{R_1 + jX_1}\right|}}}{\sqrt{\frac{P}{\left|\frac{1}{R_s + jX_s} + \frac{1}{R_2 + jX_2}\right|}}} \quad (8)$$

manipulating (8) leads to (9)

$$\frac{V_1}{V_2} = K = \frac{\sqrt{\left|\frac{(R_1 + jX_1)(R_s + jX_s)}{R_1 + jX_1 + R_s + jX_s}\right|}}{\sqrt{\left|\frac{(R_2 + jX_2)(R_s + jX_s)}{R_2 + jX_2 + R_s + jX_s}\right|}} \quad (9)$$

Note that the result is independent of the generator's power setting.

Selecting design conditions $V_1$, $V_2$, $Z_1 = R_1 + jX_1$, $Z_2 = R_2 + jX_2$, and K allows for solving for $Z_s = R_s + jX_s$ that meets the selected design conditions.

Equation (9) has complex variables in it that make it somewhat awkward to use. It can be converted into (10) after squaring both sides and manipulating the variables.

$$\frac{V_1^2}{V_2^2} = K^2 = \frac{\sqrt{R_1^2 + X_1^2}\sqrt{(R_s + R_2)^2 + (X_s + X_2)^2}}{\sqrt{R_2^2 + X_2^2}\sqrt{(R_s + R_1)^2 + (X_s + X_1)^2}} \quad (10)$$

Selecting design conditions $V_1$, $V_2$, $(R_1, X_1)$, $(R_2, X_2)$, and K allows for solving for $R_s$ and $X_s$ that meets the selected design conditions. Such solution methods are well known to those skilled in the art. For example, (10) can be solved for $R_s$ and for $X_s$ (two roots exist for both of these variables) and a set of two equations can be solved to produce explicit equations for $R_s$ and $X_s$. Design values for $R_s$ are always greater than zero and range from about 0 to 8,000 and more commonly between about 0 and 4,000 and typically will be in the range of about 100 to 2,000. Values for $X_s$ will typically be less than zero because electrosurgical procedures usually exhibit capacitive effects. Design values for $X_s$ will range from about 0 to −8,000 and more commonly will be in the range of about 0 to −4,000 and will usually be in the range of about −100 to −3,000.

Figure 9:
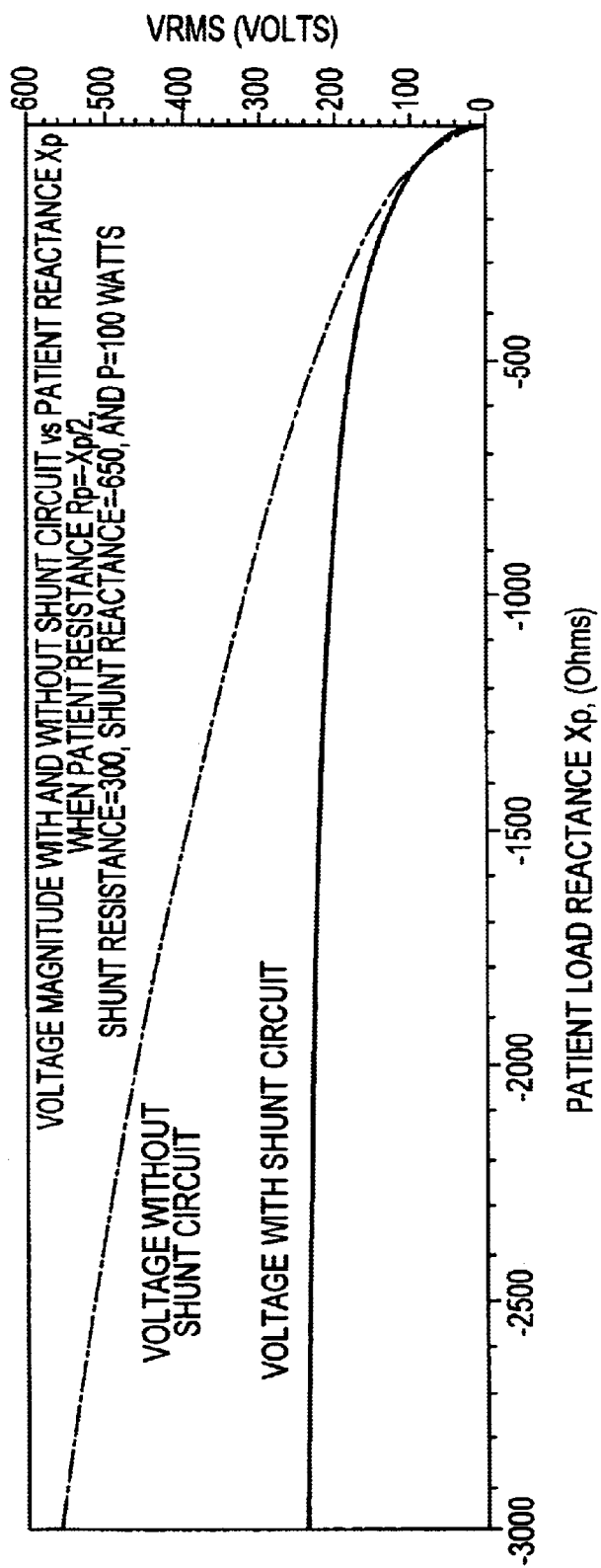
FIG. 9 shows how $V_{rms}$ varies with patient load reactance with the shunt circuit of FIGS. 6A–D and without such a shunt circuit.

FIG. 9 shows the results of one set of such calculations. The RMS voltage is plotted against $X_p$. $X_p$ is less than zero in this plot because measured data show that only very rarely does the patient reactance take on positive values, indicating that the patient load is usually capacitive.

Figure 10:
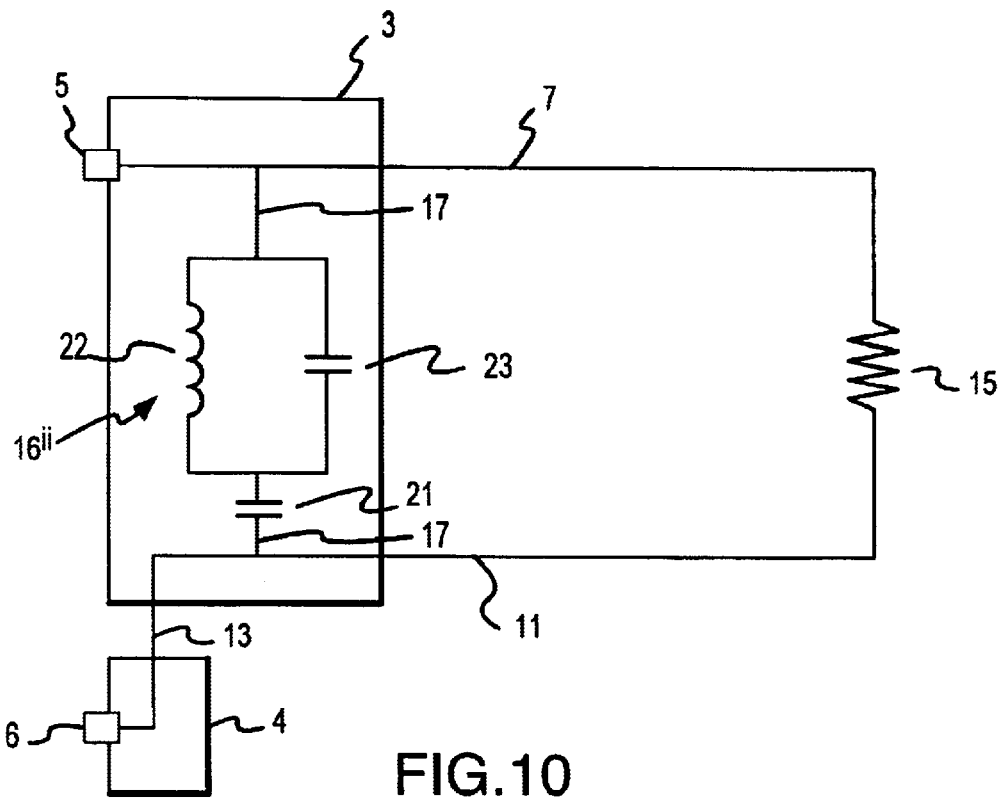
FIG. 10 schematically illustrates the use of an inductor and capacitor for the shunt circuit of FIGS. 6A–D.
Figure 11:
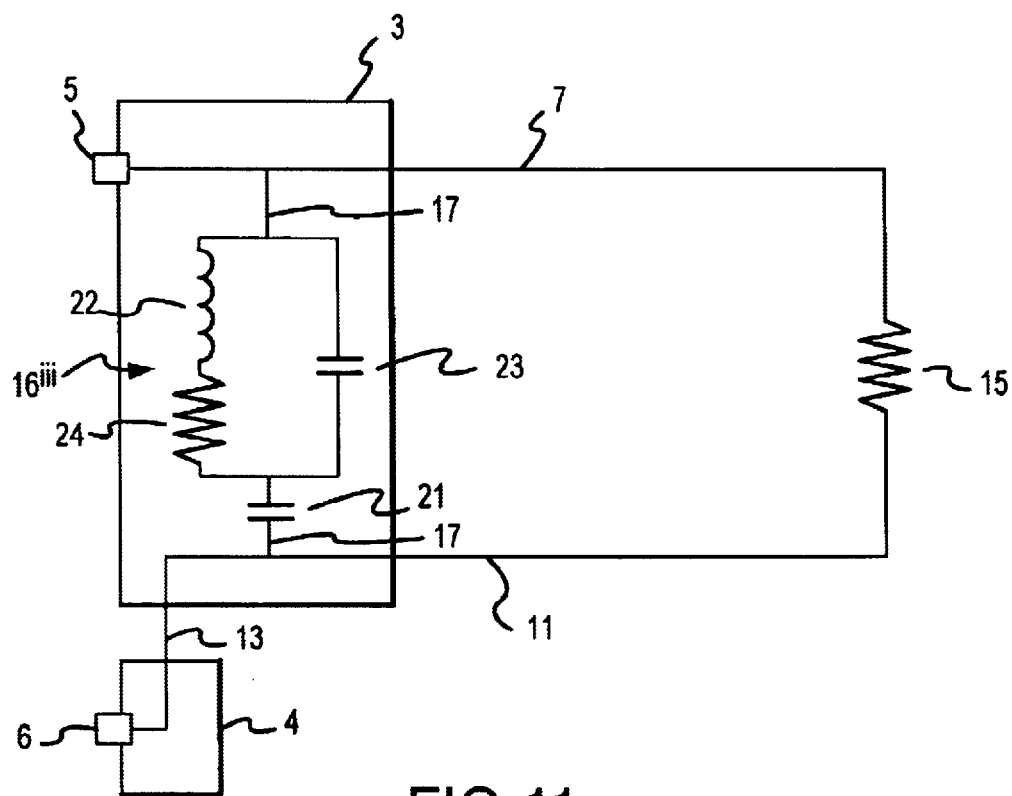
FIG. 11 schematically illustrates the use of an inductor and capacitor for the shunt circuit of FIGS. 6A–D, together with the inherent resistance of the inductor.

A variety of circuits can produce the $R_s$ and $X_s$ that come from the preceding procedure. Constraints such as cost and the desirability of having the circuit work over a range of generator output frequencies reduces the number of candidate circuits. FIG. 10 illustrates another embodiment which may be utilized by the shunt circuit 16 of FIGS. 6A–D, but which is illustrated only in relation to FIG. 6A for convenience, and which has three components that displays little sensitivity to generator output frequency over a wide range of frequencies. The circuit $16^{ii}$ contains shunt capacitor 21, shunt inductor 22, and parallel capacitor 23. This circuit $16^{ii}$ does not accurately represent the circuit that needs to be analyzed because inductors commonly have inherent capacitance and resistance. The parallel capacitor 23 may not be needed if the shunt inductor 22 has enough inherent capacitance to provide the value needed for the parallel capacitor 23, otherwise an actual capacitor will need to be present to augment the inherent capacitance of the shunt inductor 22. FIG. 11 adds the inherent resistance of the shunt inductor 22 by including shunt resistor 24 in the shunt circuit $16^{iii}$, again which may be utilized by the shunt circuit 16 of FIGS. 16A–D, but which is illustrated only in relation to FIG. 6A for convenience. Shunt resistor 24, smooths out the poles and zeros that occur near resonance that occurs with the circuit and it may not require adding a component. The shunt inductor 22 has inherent resistance that is within the range of that needed for shunt resistor 24.

Designating shunt capacitor 21 as $C_2$ and parallel capacitor 23 as $C_1$ allows the following the general approach to be used to select the values for the components in the circuit of FIG. 11.

From before, have the desired values for $R_s$ and $X_s$. Only care about matching $R_s$ and $X_s$ so do not include the patient load.

$$Z_s = \frac{1}{\frac{1}{jwL+R} - \frac{j}{wC_1}} - \frac{j}{wC_2} \tag{11}$$

The inherent R of the L is usually related to the inductance by a the Quality factor, Q;

$$Q = wL/R \tag{12}$$

Frequency is related to w by:

$$w = 2\pi f \tag{13}$$

Removing R and w from equation 27 leads to:

$$Z_s = \frac{1}{\frac{1}{2j\pi fL + 2\frac{\pi fL}{Q}} - \frac{1}{2}\frac{j}{\pi fC_1}} - \frac{1}{2}\frac{j}{\pi fC_2} \tag{14}$$

Taking the real part of $Z_s$ gives the shunt resistance $R_s$:

$$R_s = 2\frac{\pi fLQC_1^2}{2Q^2C_1L + Q^2C_1^2L^2Q^2L^2} \tag{15}$$

Taking the imaginary part of $Z_s$ gives the shunt reactance $X_s$:

$$X_s = \frac{1}{2}\frac{\frac{L(4\pi^2 f^2 LC_1C_2 - L)}{(QC_1+LQ)^2+L^2} + \frac{(QC_1+LQ)(4\pi^2 f^2 LC_1C_2Q - QC_1 - LQ)}{(QC_1+LQ)^2+L^2}}{\pi fC_2} \tag{16}$$

Now have $R_s$ and $X_s$ in terms of L, Q, $C_1$, $C_2$, and f. Select a design frequency, use equation 10 to select the desired values for $R_s$ and $X_s$, and then choose from the variety of L, Q, $C_1$, and $C_2$ that meet the design goals. If a second design frequency is selected, for example to span a range of generator output frequencies, and the corresponding second set of design $R_s$ and $X_s$, then another variable from L, Q, $C_1$, and $C_2$ can be eliminated. No explicit solution exists so graphical or other methods known to those skilled in the art are needed to select final component values. Typical values for L are between about 5 and 1000 microhenries and usually are in the range of about 10 to 100 microhenries. Q will typically be between 1 and 10. $C_1$, the parallel capacitor 23, will typically have values in the range of about 1 picofarad to 1 microfarad and will more commonly have values in the range of 0.1 nanofarad to 500 nanofarads. $C_2$ will typically have values between about 1 picofarad to 1 microfarad and will more commonly have values in the range of 0.01 nanofarad and 500 nanofarads.

The preceding equations allow selecting component values to meet any selected target values for the example shunt circuit's resistance and reactance needed to produce a desired system response. Other candidate circuits can be developed using methods known to those skilled in the art.

Figure 12:
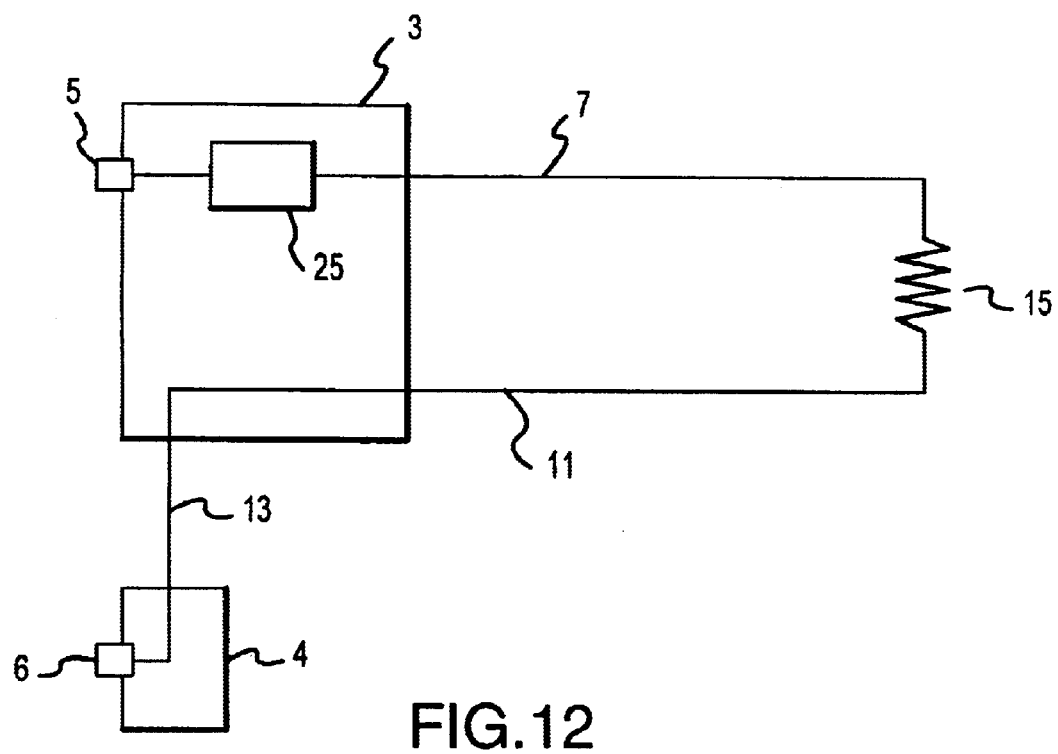
FIG. 12 schematically illustrates a series circuit in the power plug which may be utilized in relation to one or more aspects of the present invention.

FIG. 12 illustrates that a series circuit 25 can be placed in the output of generator 1. In this example the series circuit 25 is placed in the output plug 3. Series circuit 25 may contain whatever arrangement of electronic components, including passive and active components, that is needed to achieve a design objective such as compensating for the impedance of a return coupler of the type addressed in relation to FIGS. 13, 14, and 16A–18 below.

Figure 13:
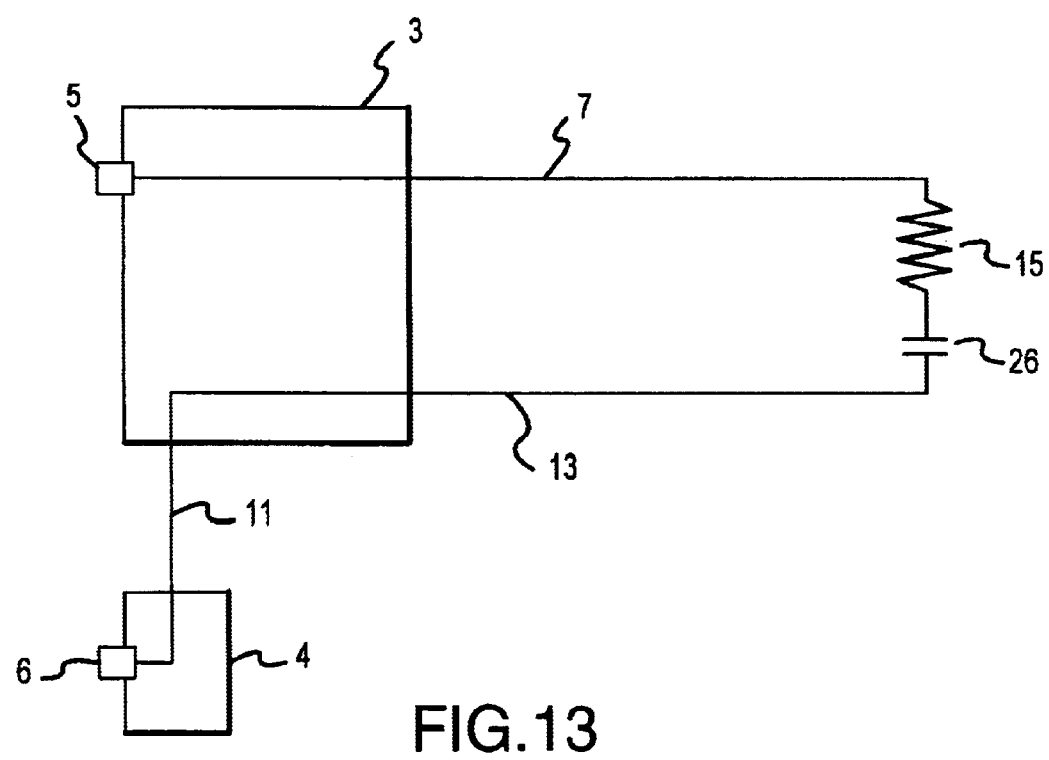
FIG. 13 schematically illustrates a return coupler for an electrosurgical accessory or assembly in accordance with one or more principles of the present invention.
Figure 14:
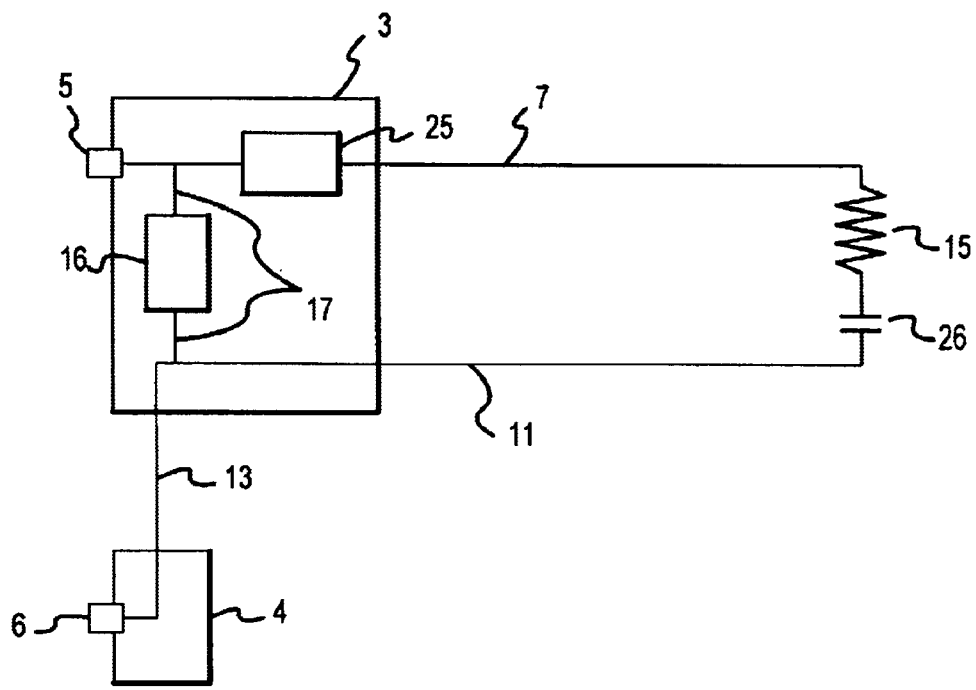
FIG. 14 schematically illustrates the return coupler of FIG. 13 in conjunction with the shunt circuit of FIG. 6A and the compensating series circuit of FIG. 12.
Figure 15:
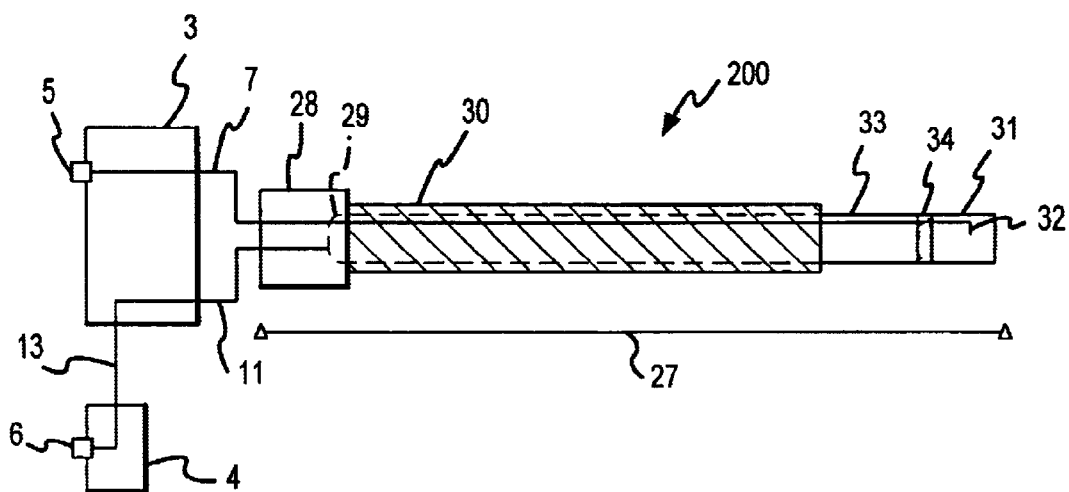
FIG. 15 schematically illustrates a prior art bipolar probe with a return electrode.

FIG. 13 illustrates schematically the presence of a return coupler 26 which is discussed in more detail below in relation to FIGS. 16A–18, and how it is in series with the patient load 15. FIG. 14 illustrates how the shunt circuit 16 can be combined with the return coupler 26 and that series circuit 25 can also be used at the same time. The shunt circuit 16 can be designed to work with the total impedance resulting from the presence of series circuit 25, the patient 15, and the return coupler 26. These three elements produce a single lumped impedance that can be interpreted as the lumped design resistance, $R_p$, and reactance, $X_p$ used in, for example, equation 4.

Figure 16A:
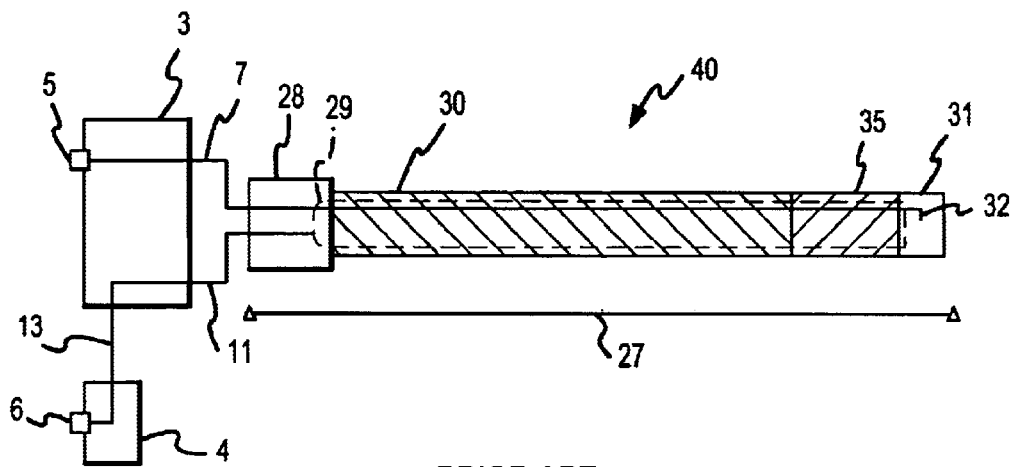
FIG. 16A schematically illustrates a bipolar probe with a return coupler in accordance with one or more principles of the present invention.
Figure 16B:
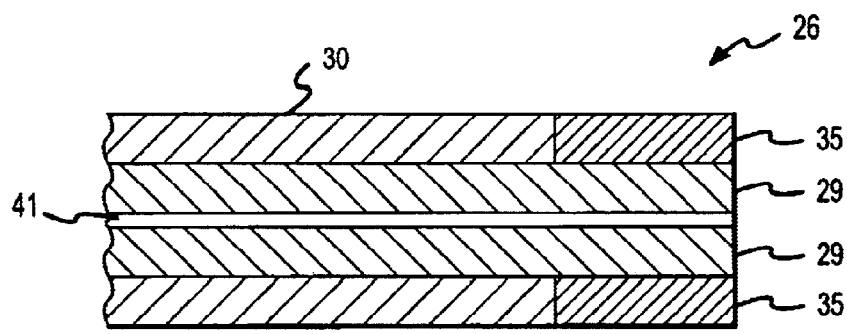
FIG. 16B is an enlarged cross-sectional view of the return coupler of FIG. 16A.

FIGS. 16A–B illustrate an electrosurgical accessory 40 that includes a probe assembly 27. The probe assembly 27 is interconnected with the output connector plug 3 by the output line 7, and is interconnected with the return connector plug 4 by the return line 11 and supplemental return line 13. The output connector plug 3 of the accessory 40 again interfaces with the output connector 5 of the generator 1, while the return connector plug 4 of the accessory 40 again interfaces with the return connector 6 of the generator 1.

The probe assembly 27 of the accessory 40 includes a probe handle 28 (e.g., for engagement by a surgeon), a probe shaft 29 which extends therefrom, and an active electrode assembly 31 which extends beyond an end of the probe shaft 29 and which includes an active electrode 32. All of the probe shaft 29 is insulated. None of it is exposed to conductive liquid. In this regard, the probe shaft 29 is insulated along part of its length with typical probe shaft insulation 30, as shown in FIG. 16A. All or part of the probe shaft 29, including any portions that are not covered with typical probe shaft insulation 30, is covered with return coupler insulation 35. The return coupler insulation 35 and the probe shaft 29 collectively define the return coupler 26 which provides an initial return path from the patient to the generator 1. Return coupler insulation 35 is selected to allow energy transfer by electric fields to the probe shaft 29, which then transfers the energy via conduction to the return line 11, supplemental return line 13, and return connector plug 4 to the generator 1. The active electrode 32 is insulated from the probe shaft 29 using a suitable means, such as an active electrode standoff insulator (not shown).

FIGS. 16A–B illustrate that the probe shaft 29 is a solid, and that the return coupler insulation 35 is effectively a layer which is annularly disposed about an end portion of the probe shaft 29 (e.g., concentric with the probe shaft 29). In this case the output line 7 (which may be insulated) may be directed through a channel 41 formed in the probe shaft 29 (FIG. 16B).

The return coupler insulation 35 may be applied in a variety of ways. The insulation may be a coating that is applied to the probe shaft 29. Alternatively, the return coupler insulation 35 may be a component, such as a dielectric tube, that is slipped over the probe shaft 29. Similarly, one or more components made from dielectrics may be applied to the tube. When components are used to form the return coupler insulation 35, the gap between it/them and the probe shaft 29 is filled with a gap-filling conductive material (not shown) such as conductive epoxy. The gap-filling material may also be used to hold the components in place, as would be the case if a conductive epoxy is used. A suitable component is a ceramic tube composed primarily of barium titanate with a wall thickness of about 30 mils and an area of about 0.2 square inches.

The return coupler insulation 35 must have a combination of thickness, dielectric constant, dielectric strength, and area such that it withstands the electric field voltages without breaking down and has a low enough impedance to allow adequate energy flow. The exposed area of the surrounding insulation 35 will also affect the impedance of the return coupler 26. A variety of insulation designs may be used, but they all have in common the ability to withstand the voltage and have suitably low impedance. The preferred embodiment will withstand voltages exceeding 1,000 volts peak to peak, preferably withstand 2,000 volts peak to peak, and more preferably withstand 5,000 volts peak to peak. The impedance of the return coupler 26 is preferably less than about 800 ohms, with values less than 500 ohms being preferred. An impedance of 300 or even 200 ohms or less is even more preferred.

To meet the twin goals of high voltage withstand strength and low impedance, both the dielectric constant and the dielectric strength need to be jointly maximized for the return coupler insulation 35. The product of these values is the dielectric product (DP). Dielectric constant is dimensionless. Dielectric strength is measured in volts/mil. DPs greater than 2,000 are preferred, and DPs greater than 4,000 and even 8,000 are even better. A variety of materials with large DPs are candidate materials, but the preferred embodiment uses either titanium dioxide or barium titanate. Powder forms of these materials are used in which the particle sizes are less than about 40 microns to less than 0.05 microns. Different sizes can be blended together. These substances are combined with a polymer or adhesive to form an insulating coating material. An example of such a material is epoxy.

As an example, the following method produces suitable return coupler coatings 35. Barium titanate powder that passes through a 325 mesh screen is blended with barium titanate powder with about 0.05 micron size particles. The 325 mesh particles constitute about 60–80 per cent of the particles. The particles are blended together and then mixed with acetone to make a slurry using a rotating mixer. A ratio of about 70 gm of powder: 30–70 ml of acetone is used. The mixing process continues until the slurry has become thicker as the acetone evaporates. The evaporation step lasts about 1 hour at room temperature and may be shortened to 5 minutes if the mixture is heated. A two part epoxy with a suitable dielectric strength is mixed and then added to the acetone-barium titanate mixture while the rotating mixer is running. About 20 grams of epoxy are mixed with 60 grams of powder. The powder constitutes about 30–40 volume percent of the powder:epoxy final mixture. Powder volumes greater than this are desirable if they can be blended and applied. The powder-acetone-epoxy mixture is applied by dipping a metal probe shaft into the mixture. Multiple dips, about 4 to 5, are used to make a coating that is 10 mils or less thick and preferably 5–7 mils thick. About 2 minutes elapses between dips as the acetone evaporates, which may be aided using hot air. After the final dip, the epoxy is cured at elevated temperature. Example curing cycles are 50° C. for about 10 hours and 180° C. for 2 hours. This process results in return couplers 26 having dielectric constants of between about 20 and 50, with the higher values occurring with the higher concentrations of barium titanate. The resulting impedances are between about 100 and 1,000 ohms when return coupler areas of between about 0.2 and 0.75 square inches are used and the RF frequency is in the range of about 200 kilohertz to 800 kilohertz.

Figure 17:
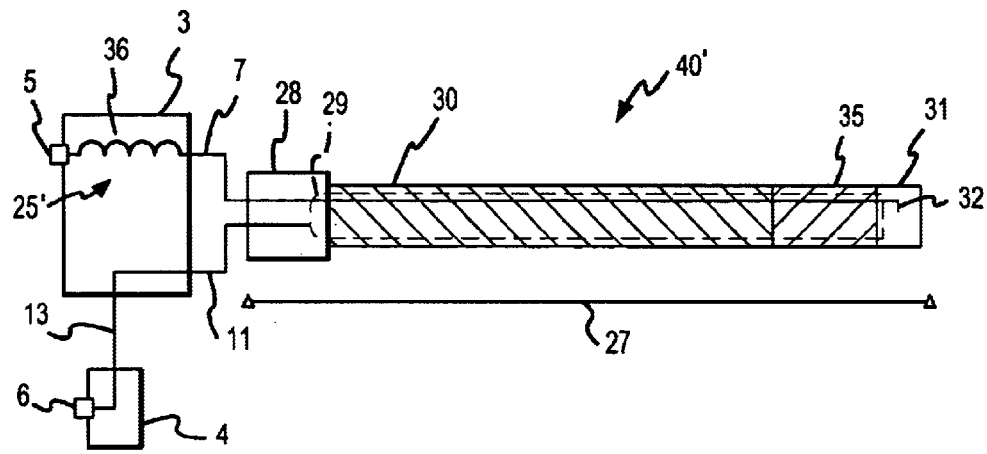
FIG. 17 schematically illustrates a bipolar probe with a return coupler with a compensating inductor in accordance with one or more principles of the present invention.

FIG. 17 illustrates a variation of the accessory 40 of FIG. 16A by using a compensating inductor 36 to offset the impedance of the return coupler 26, and thereby a "single prime" designation is used to identify the accessory 40'. This is the preferred means of using a series circuit 25' to offset the return coupler's impedance, although other means exist and using a compensating inductor 36 is not required. The series circuit 25' is designed so that the compensating inductor 36 is in series resonance with the return coupler 26. Selecting the design specifications for the compensating inductor 36 is known art once the impedance of the return coupler 26 has been specified along with a design frequency. Other sources of series capacitance, such as those associated with tissue interactions with the active electrode 32 during electrosurgical processes do not need to be taken into account to provide a beneficial result from including a compensating inductor 36, although taking these interactions into account is acceptable. The compensating inductor 36 is preferably located in the output connector plug 3. This plug 3 may have features such as sealed through holes, heat sinks, or fins to aid in cooling it. Such features can also be incorporated into the plug as ergonomic aids to facilitate identifying it, plugging it into the generator 1, or removing it from the generator 1.

Figure 18:
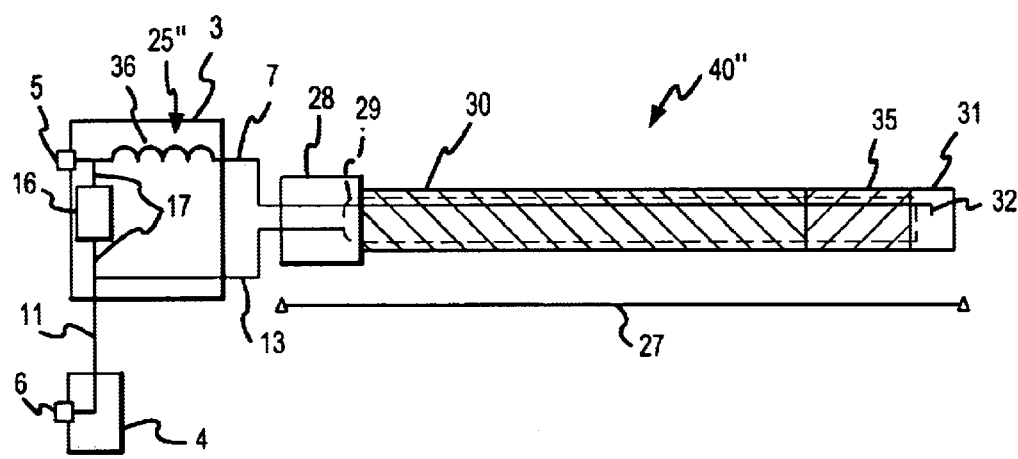
FIG. 18 schematically illustrates a bipolar probe with a return coupler with a compensating inductor and a shunt circuit in accordance with one or more principles of the present invention.

FIG. 18 illustrates a variation of the accessory 40' of FIG. 17 by using a shunt circuit 16 in combination with a return coupler 26 and a compensating inductor 36, and thereby a "double prime" designation is used to identify the accessory 40'. The shunt circuit 16 and the compensating inductor 36 are both preferably located in the output connector plug 3. The shunt circuit 16 is designed with a load resistance, $R_p$, and reactance, $X_p$, that includes the contributions from one or more of the return coupler 26, the compensating inductor 36, and tissue interactions that occur during electrosurgical procedures.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed is:

1. An electrosurgical assembly which interfaces with a generator for executing a first electrosurgical procedure and which comprises:

an output assembly which is at least operatively interconnectable with said generator;

an active electrosurgical element which is operatively interconnected with said output assembly and which is interfaceable with a first portion of a patient during said first electrosurgical procedure;

a return path element, wherein at least part of said return path element is interfaceable with a second portion of said patient during said first electrosurgical procedure, said second portion being different from said first portion;

a return assembly which is operatively interconnected with said return path element and further which is at least operatively interconnectable with said generator; and a shunt circuit between said output and return assemblies, wherein said shunt circuit comprises at least one passive element and is devoid of any active elements, and wherein said shunt circuit produces a reactive load.

2. An electrosurgical assembly, as claimed in claim 1, wherein:

said generator comprises an output connector and a return connector, said output assembly comprises an output plug which is detachably interconnectable with said output connector and an output line which is disposed between said output plug and said active electrosurgical element, and wherein said return assembly comprises a return plug which is detachably interconnectable with said return connector and a return line which is disposed between said return plug and said return path element.

3. An electrosurgical assembly, as claimed in claim 1, wherein:

said active electrosurgical element comprises at least one active electrode, wherein each said electrode has at least one patient interface surface, and wherein each said patient interface surface is selected from the group consisting of a curved surface and a flat surface.

4. An electrosurgical assembly, as claimed in claim 1, wherein:

said active electrosurgical element is selected from the group consisting of one or more blades, hooks, balls, spatulas, loops, pins, wireforms, tubes, and tubes with fluid passageways.

5. An electrosurgical assembly, as claimed in claim 1, wherein:

said electrosurgical assembly is selected from the group consisting of a monopolar configuration and a bipolar configuration.

6. An electrosurgical assembly, as claimed in claim 1, wherein:

said return path element comprises a return coupler, wherein said return coupler comprises a first dielectric material which interfaces with said patient during said first electrosurgical procedure, wherein said return coupler further comprises a first return conductor which interfaces with said first dielectric material in such a manner that energy is returned to said generator first through said first dielectric material and then to said first return conductor.

7. An electrosurgical assembly, as claimed in claim 1, wherein:

said patient defines a patient impedance load, and wherein said shunt circuit is disposed in parallel with said patient impedance load.

8. An electrosurgical assembly, as claimed in claim 1, wherein:

said shunt circuit comprises at least one electronic element which is selected from the group consisting of capacitors, inductors, resistors and any combination thereof.

9. An electrosurgical assembly, as claimed in claim 1, wherein:

said shunt circuit includes a single electronic element.

10. An electrosurgical assembly, as claimed in claim 1, further comprising:

a user handle, wherein said shunt circuit is disposed in a part of said electrosurgical assembly other than said user handle.

11. An electrosurgical assembly, as claimed in claim 1, wherein:

said output assembly comprises an output plug which detachably interfaces with said generator, wherein said shunt circuit is disposed within said output plug.

12. An electrosurgical assembly, as claimed in claim 1, wherein:

said return assembly comprises a return plug which detachably interfaces with said generator, wherein said shunt circuit is disposed within said return plug.

13. An electrosurgical assembly, as claimed in claim 1, further comprising:

a handle and a probe which extends from said handle and supports at least said active electrosurgical element, wherein said output assembly comprises an output plug which detachably interfaces with said generator and an output line which is disposed between said active electrosurgical element and said output plug, wherein at least a first portion of said output line extends between said output plug and said handle, wherein said return assembly comprises a return plug which detachably interfaces with said generator and a return line which extends from said return plug, through said output plug, and at least toward said return path element, wherein a first portion of said return line is disposed between said output plug and said handle, wherein a second portion of said return line is disposed between said output and return plugs, and wherein said shunt circuit extends between said first portion of said output line and said first portion of said return line.

14. An electrosurgical assembly, as claimed in claim 1, wherein:

said output assembly comprises an output plug and an output line which is disposed between said active electrosurgical element and said output plug, wherein said return assembly comprises a return plug and a return line which is disposed between said return plug and said return path element, wherein said electrosurgical assembly further comprises an in-line adapter which detachably interconnects with said generator, wherein said output and return plugs detachably interface with said in-line adapter, and wherein said shunt circuit is disposed within said adapter.

15. An electrosurgical assembly, as claimed in claim 1, wherein:

said electrosurgical generator is a constant power generator, and wherein said electrosurgical assembly comprises means for achieving an at least substantially constant voltage operational mode for said first electrosurgical procedure, and wherein said means for achieving comprises said shunt circuit.

16. An electrosurgical assembly, as claimed in claim 1, further comprising:

means for limiting a maximum voltage applied to said patient, wherein said means for limiting comprises said shunt circuit.

17. An electrosurgical assembly, as claimed in claim 1, wherein:

said shunt circuit comprise means for limiting a voltage output variance by said electrosurgical assembly throughout said first electrosurgical procedure to no more than about 15%.

18. An electrosurgical assembly, as claimed in claim 1, wherein:

an impedance of said patient during said first electrosurgical procedure is within a first impedance range from about 500 ohms to about 2,000 ohms, and wherein said shunt circuit comprises means for limiting a voltage output variance by said electrosurgical assembly throughout said first impedance range to no more than about 15%.

19. An electrosurgical assembly, as claimed in claim 1, wherein:

a configuration of said electrosurgical assembly allows said first electrosurgical procedure to be selected from the group consisting of cutting, coagulation, desiccation, fulguration, ablation, and tissue shrinkage.

20. An electrosurgical assembly which interfaces with a generator for executing a first electrosurgical procedure and which comprises:

an output assembly which is at least operatively interconnectable with said generator;

an active electrosurgical element which is operatively interconnected with said output assembly and which is interfaceable with a first portion of a patient during said first electrosurgical procedure;

a return path element which is interfaceable with a second portion of said patient during said first electrosurgical procedure, said second portion being different from said first portion;

a return assembly which is operatively interconnected with said return path element and further which is at least operatively interconnectable with said generator; and a single passive capacitor electrically interconnecting said output and return assemblies.

* * * * *